United States Patent
Kobayashi et al.

(10) Patent No.: US 9,750,924 B2
(45) Date of Patent: Sep. 5, 2017

(54) ADHESIVE PATCHING AID FOR MICRONEEDLE ADHESIVE SKIN PATCH

(75) Inventors: Katsunori Kobayashi, Kagawa (JP); Hidetoshi Hamamoto, Kagawa (JP)

(73) Assignee: MEDRx Co., Ltd., Higashikagawa (JP)

(*) Notice: Subject to any disclaimer, the term of this patent is extended or adjusted under 35 U.S.C. 154(b) by 340 days.

(21) Appl. No.: 13/574,496

(22) PCT Filed: Jan. 20, 2011

(86) PCT No.: PCT/JP2011/000282
§ 371 (c)(1),
(2), (4) Date: Sep. 4, 2012

(87) PCT Pub. No.: WO2011/089907
PCT Pub. Date: Jul. 28, 2011

(65) Prior Publication Data
US 2013/0006187 A1   Jan. 3, 2013

(30) Foreign Application Priority Data
Jan. 22, 2010 (JP) .................... 2010-012620

(51) Int. Cl.
A61M 5/32   (2006.01)
A61M 37/00  (2006.01)
A61M 25/02  (2006.01)

(52) U.S. Cl.
CPC .......... *A61M 37/0015* (2013.01); *A61M 2025/0253* (2013.01); *A61M 2037/0023* (2013.01); *A61M 2037/0046* (2013.01); *A61M 2037/0061* (2013.01)

(58) Field of Classification Search
CPC ............ A61M 37/00; A61M 5/158; A61M 2037/0023; A61M 2037/0046; A61M 2037/0061; A61M 2025/0253; A61M 37/0015; A61M 5/00
USPC ............ 604/173, 174, 180, 22, 191, 272; 600/309, 183, 200
See application file for complete search history.

(56) References Cited

U.S. PATENT DOCUMENTS

2003/0065294 A1   4/2003 Pickup et al.
2008/0114298 A1*  5/2008 Cantor et al. ........... 604/117
(Continued)

FOREIGN PATENT DOCUMENTS

| CN | 101076367 A | 11/2007 |
| JP | 2005-087519 A | 4/2005 |
| JP | 2008-520369 A | 6/2008 |

(Continued)

OTHER PUBLICATIONS

Kobayashi et al. (WO 2009/107806 A2, Google English translation), Sep. 3, 2009.*
(Continued)

*Primary Examiner* — Emily Schmidt
*Assistant Examiner* — Tiffany Legette-Thompson
(74) *Attorney, Agent, or Firm* — Leydig, Voit & Mayer, Ltd.

(57) ABSTRACT

The invention provides an applicator that holds a microneedle to facilitate puncture of the skin and includes an assisting tool as a supporting base to set the microneedle and an adhesive sheet such as a tape and the like, on the side face of the assisting tool to enable close adhesion of the microneedle puncturing the skin.

14 Claims, 21 Drawing Sheets

(56) References Cited

U.S. PATENT DOCUMENTS

2009/0198189 A1   8/2009   Simons et al.
2012/0184916 A1   7/2012   Kobayashi et al.

FOREIGN PATENT DOCUMENTS

| JP | 2008-543527 A | 12/2008 |
| JP | 2009-072270 A | 4/2009 |
| WO | WO 03/074102 A2 | 9/2003 |
| WO | WO 2006/055795 A1 | 5/2006 |
| WO | WO 2006/062848 A1 | 6/2006 |
| WO | WO 2007/002521 A2 | 1/2007 |
| WO | WO 2007124411 A1 * | 11/2007 |
| WO | WO 2008/069566 A1 | 6/2008 |
| WO | WO 2008/091602 A2 | 7/2008 |
| WO | WO 2009/107806 A2 | 9/2009 |

OTHER PUBLICATIONS

European Patent Office, Extended European Search Report in European Patent Application No. 11734514.0 (Jun. 4, 2013).
Japanese Patent Office, International Search Report in International Patent Application No. PCT/JP2011/000282 (Feb. 15, 2011).

* cited by examiner (1) side view (2) bottom view a) applicator Nos. 1 - 15

NICHIBAN NICETACK NWR b) applicator Nos. 16 - 17

NICHIBAN NICETACK NWR a)

NICHIBAN NICETACK NW transversal case ↓ b)

NICHIBAN NICETACK NW

ADHESIVE PATCHING AID FOR MICRONEEDLE ADHESIVE SKIN PATCH

CROSS-REFERENCE TO RELATED APPLICATIONS

This patent application is the U.S. national phase of International Patent Application No. PCT/JP2011/000282 filed Jan. 20, 2011, which claims the benefit of Japanese Patent Application No. 2010-012620, filed Jan. 22, 2010, which are incorporated by reference in their entireties herein.

TECHNICAL FIELD

The present invention relates to an assisting tool to accurately adhere a microneedle patch to the skin. More particularly, it relates to an embankment-shaped assisting tool which contains and holds a microneedle patch.

BACKGROUND ART

As a method for transdermal administration of a drug, application of a solution or ointment to the skin surface and a transdermal preparation in the form of a patch have conventionally been used. At present, however, in an attempt to increase the skin permeability of a drug, it has been tried to topically destroy the stratum corneum with small needles (microneedles or micropins) to forcedly deliver the drug to the dermal layer.

As the material of a microneedle used to puncture the skin, metals, various resins and the like are used. To suppress disorders of the skin, biodegradable materials tend to be used often. However, when the material of the microneedle is a biodegradable resin and the angle of puncture relative to the skin is a little off perpendicular, the small needles of the microneedle break or bend easily, making it difficult to appropriately puncture the skin (patent document 1).

Thus, various applicators (insertion tools) used to perpendicularly puncture the skin with a microneedle have been developed (patent document 2). Recently, those enabling easy and simple puncture of the skin by simply pressing with finger(s) have been developed (patent documents 3, 4).

However, when a microneedle patch that can be fixed by adhesion to the skin with a tape was produced and actually used, adhesion to the skin was clarified to be insufficient during removal of the assisting tool of the patch since the microneedle is lifted up or separated from the skin.

It has also been clarified that transfer of a tape adhered to the applicator with an adhesive onto the skin sometimes fails. To solve this, an adhesive having a weak adhesion power may be used between the applicator and the tape; however, a dilemma ultimately occurs in that it cannot stand distribution and the like.

Furthermore, certain insertion of needles into the skin was sometimes unavailable. Whether or not needles can be inserted into the skin is considered to depend on whether the stress of the microneedle to the skin exceeds a certain level. However, the conventional method of simply pressing with finger(s) problematically cannot determine the stress.

As mentioned above, it is further necessary to study a holding tool and a tape for a microneedle patch to form a microneedle patch and afford a practical product.

PATENT LIST

Patent Documents

[patent document 1] WO2008/069566
[patent document 2] JP-A-2008-543527
[patent document 3] JP-A-2008-520369
[patent document 4] JP-A-2009-72270

SUMMARY OF THE INVENTION

Problems to be Solved by the Invention

The present invention provides an assisting tool that enables accurate fixing of a microneedle patch to the skin by puncture. In addition, it aims to provide a portable applicator wherein the assisting tool of the present invention is set (applicator to hold a microneedle patch).

Means of Solving the Problems

The present inventors have heretofore studied applicators and devices to insert a microneedle perpendicularly into the skin, and produced chip-like applicators having a tubular device or a concave part (Japanese patent application Nos. 2008-051335, 2009-184683, 2009-202328). In the above-mentioned inventions of the applicators, a microneedle is perpendicularly punctured into the skin by utilizing perpendicular elevation of the skin caused by pressing of a tubular member against the skin. However, further studies were necessary to fix a patchized microneedle to the skin by adhesion. Therefore, the present inventors have made various studies and found that conventional defects can be markedly improved by appropriately selecting a supporting base to place and hold a microneedle. That is, it has been found in the present invention that a microneedle can be efficiently punctured into the skin by using an applicator having an assisting tool (supporting base for microneedle) as shown in FIGS. 5 and 8, as well as closely adhered to the skin with a tape.

The present invention has been completed by conducting further studies based on these findings, and the summary thereof is as follows.

(1) An applicator for a microneedle for puncturing skin with the microneedle, comprising an assisting tool as a supporting base to set the microneedle.
(2) The applicator of the above-mentioned (1), wherein the assisting tool has a height of 0.5-10 mm.
(3) The applicator of the above-mentioned (1), wherein the assisting tool has a height of 2-7 mm.
(4) The applicator of any of the above-mentioned (1)-(3), wherein the assisting tool has a shape of an ingot, a circular truncated cone or a polygonal truncated pyramid.
(5) The applicator of any of the above-mentioned (1)-(4), wherein the above-mentioned assisting tool has a shape of an ingot, and a dip angle of the section of 130-175°.
(6) The applicator of any of the above-mentioned (1)-(5), wherein the above-mentioned section has a dip angle of 145-175°.
(7) The applicator of any of the above-mentioned (1)-(6), which has a side wall(s) at the periphery of the above-mentioned assisting tool.
(8) The applicator of any of the above-mentioned (1)-(7), wherein the above-mentioned side wall(s) at the periphery of the assisting tool has a cylindrical shape, rectangular hollow section shape (Japanese "masu"-shaped), or a pair of side plates.
(9) The applicator of any of the above-mentioned (1)-(8), wherein the above-mentioned a pair of side plates are a part of the cylindrical shape or a part of the rectangular hollow section shape (Japanese "masu"-shaped).

(10) The applicator of any of the above-mentioned (1)-(9), wherein the above-mentioned a part of the rectangular hollow section shape (Japanese "masu"-shaped).
is a pair of flat plates.
(11) The applicator of any of the above-mentioned (1)-(10), wherein the height of the assisting tool is lower than that of the side wall(s) and the tip of the microneedle does not exceed the side wall(s) even when a microneedle is set.
(12) The applicator of any of the above-mentioned (1)-(11), which has a circular or rectangular shape when the above-mentioned assisting tool is set.
(13) The applicator of the above-mentioned (12), wherein the above-mentioned circular shape has a diameter of 2-5 cm.
(14) The applicator of any of the above-mentioned (1)-(13), wherein the above-mentioned rectangle has a size of 3-7 cm in each of the length and width.
(15) The applicator of any of the above-mentioned (1)-(14), wherein a microneedle and a tape are set.
(16) The applicator of any of the above-mentioned (1), wherein the above-mentioned applicator comprises
a) an assisting tool on which the microneedle and a tape are set,
b) a resin flat plate on which the assisting tool is set and
c) a pair of side plates, wherein the side plates have a height higher than that of the assisting tool.
(17) The applicator of any of the above-mentioned (16), wherein the tape and the microneedle are set on the assisting tool, and the microneedle is carried on the adhesive face of the tape.
(18) The applicator of any of the above-mentioned (16) or (17), wherein the above-mentioned resin flat plate has a rectangular shape of 3-7 cm.
(19) The applicator of any of the above-mentioned (16)-(18), wherein the assisting tool has an ingot-like shape.
(20) The applicator of any of the above-mentioned (16)-(19), wherein the above-mentioned side plates has a height of 2-15 mm.
(21) The applicator of any of the above-mentioned (16)-(20), wherein the above-mentioned assisting tool has a height of 2-7 mm, and the height of the side plate is higher by 2-3 mm than that of the assisting tool.
(22) The applicator of any of the above-mentioned (16)-(21), wherein the above-mentioned ingot-shape assisting tool has a section having a trapezoid with a dip angle of 175-145°.
(23) The applicator of any of the above-mentioned (16)-(22), wherein the edge of the above-mentioned ingot-shape assisting tool overlaps with the edge of the above-mentioned resin flat plate.
(24) The applicator of any of the above-mentioned (16)-(23), wherein the above-mentioned ingot-shape assisting tool has a section having a trapezoid with a dip angle of 166-145°.
(25) The applicator of any of the above-mentioned (16)-(24), wherein the above-mentioned assisting tool, resin flat plate and side plate are integrally molded with a resin.

Effect of the Invention

The present invention relates to an ingot-shape assisting tool (supporting, base) for retaining a pin-frog-shaped microneedle and an applicator comprising the same. By placing a microneedle on the base of the assisting tool of the present invention, the microneedle can be used for efficient puncture, and the tape holding the microneedle can also be used to closely adhere the microneedle to the skin surface. In addition, the transfer from the tape applicator to the skin can be ensured. Moreover, the stress of the microneedle onto the skin can be easily designed, which ensures insertion of the microneedle into the skin. Therefore, even an ordinary people can efficiently puncture the skin with the microneedle by removing a protection cover of the applicator and pressing the microneedle with a finger(s), thereby simultaneously adhering same closely to the skin surface with a tape.

DESCRIPTION OF EMBODIMENTS

Hereinafter, the present invention will be further explained in detail with reference to preferable aspects shown in the appended drawings.

Figure 1:
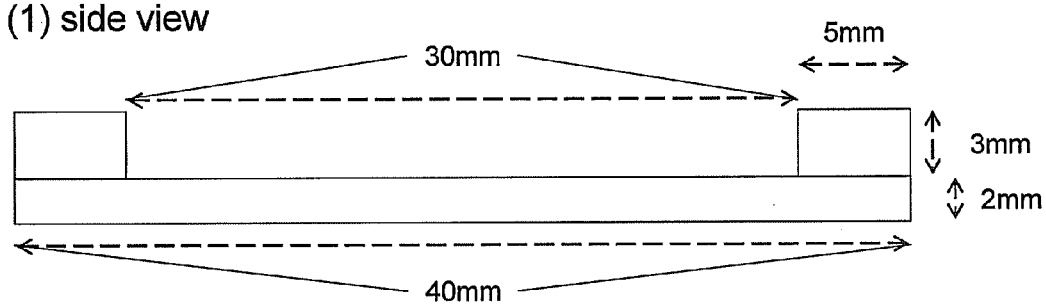
FIG. 1 shows one embodiment (Japanese "geta"-shaped applicator) of the applicator of the present invention before setting an assisting tool (supporting base for microneedle).
Figure 1:
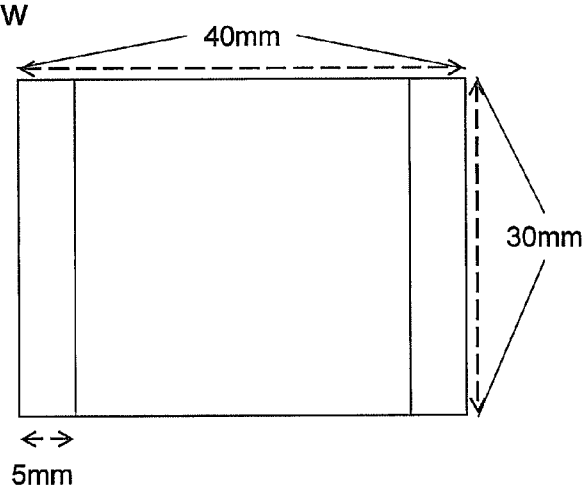

FIG. 1 is a sectional view showing one embodiment of the applicator used in the present invention. FIG. 1 is the applicator before setting an assisting tool consisting of a hard resin flat plate to place a microneedle thereon and two hard resin side plates.

As the "hard resin flat plate" in the present invention, a hard member which is not deformed much even when pressed with finger(s) is preferably used. Examples of the hard member include those made of various known materials. For example, it is not particularly limited as long as it is a synthetic resin with at least a certain thickness. Examples of the material include hard resins such as polyethylene resin, polypropylene resin, polyvinyl chloride resin, acrylic resin, poly(ethylene terephthalate) resin, polystyrene resin, acrylonitrile-butadiene-styrene copolymer, polycarbonate resin, polyamide resin, fluororesin, polybutylene terephthalate resin and the like.

Figure 4:
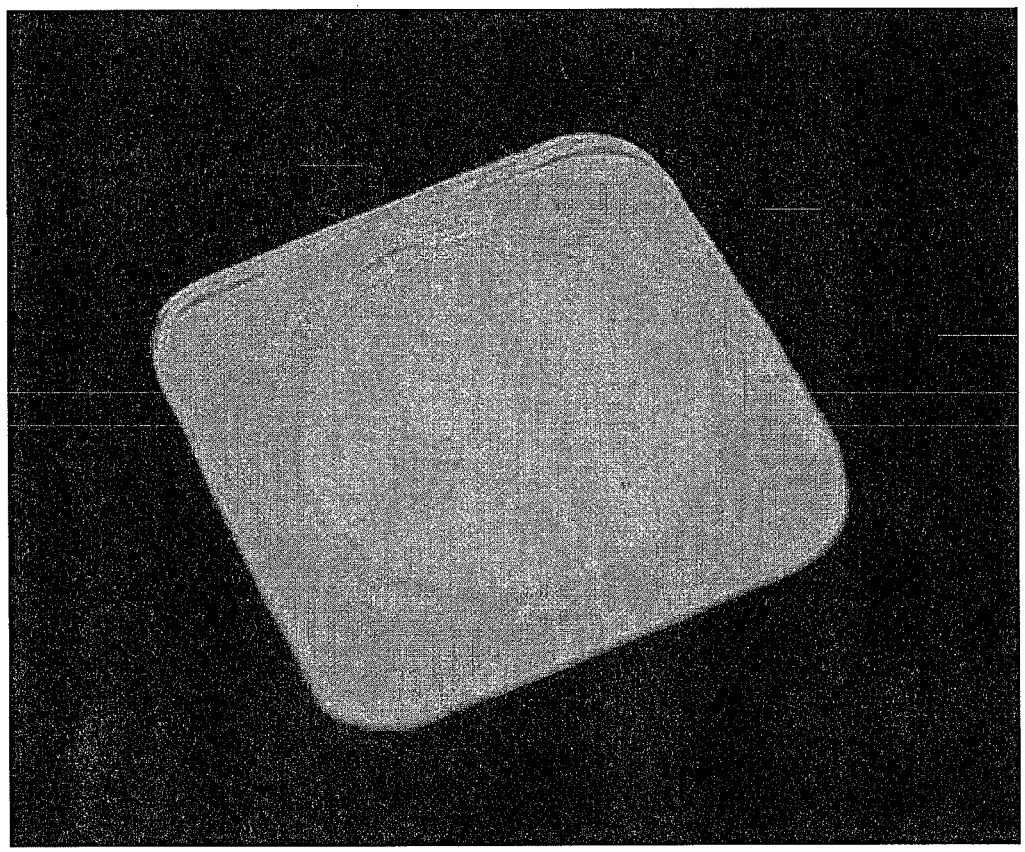
FIG. 4. shows one embodiment of the "wappen"-shaped applicator obtained by the test method of FIG. 2.

The shape of the hard resin flat plate is not particularly limited, is sufficient as long as a microneedle can be housed, and can be appropriately adjusted according to the size of the microneedle. For example, a rectangle having each of the length and width of 3-7 cm and a circular shape having a diameter of 3-7 cm can be used. For example, a rectangle of 3×4 cm as shown in FIG. 1, and a square of about 3 cm one side having a circular concave part as shown in FIG. 4 can be used.

Figure 3:
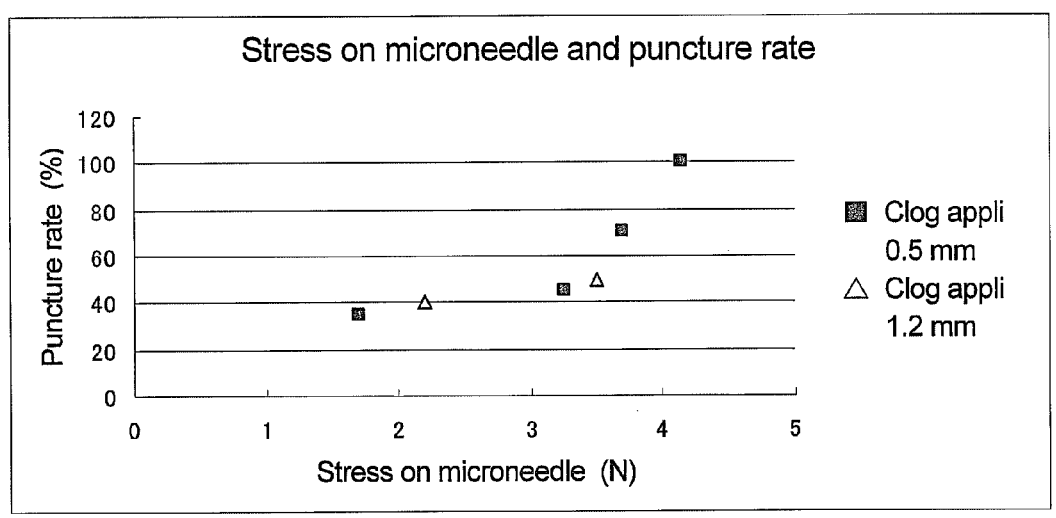
FIG. 3 shows the puncture rate of the microneedle and the change of stress obtained by the test method of FIG. 2 and using the Japanese "geta"-shaped applicator of the present invention.
Figure 13:
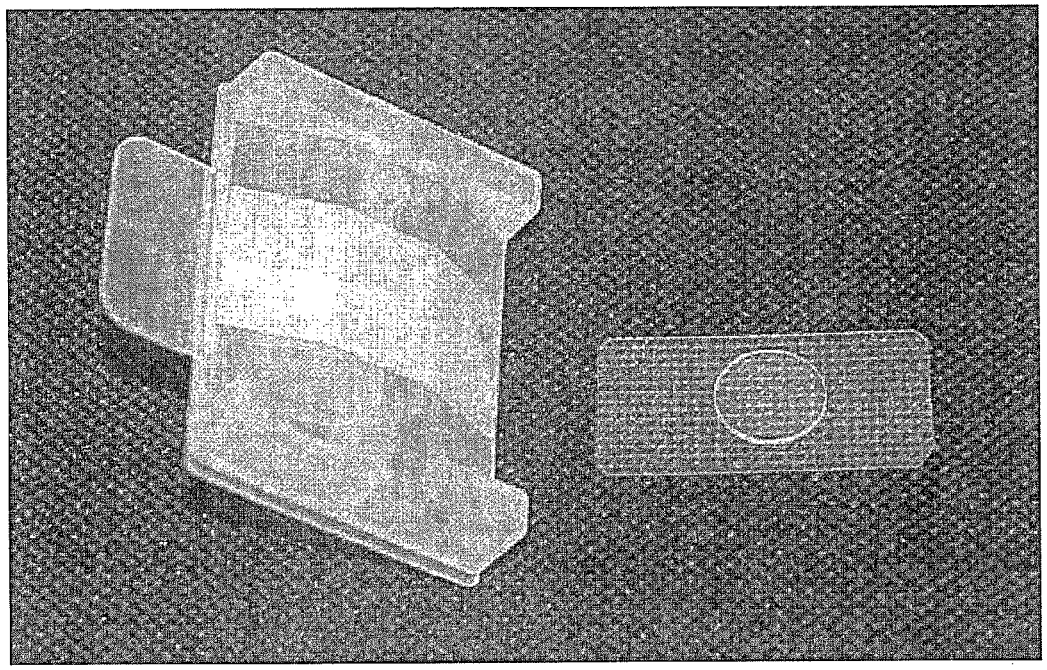
FIG. 13 is a perspective view (photograph) of the Japanese "geta"-shaped applicator of the present invention wherein the applicator shown in FIG. 12 is produced by integral molding of a resin, wherein the assisting tool has a double-faced adhesive tape, and on the right side thereof is shown a tape having a microneedle (dummy) adhered on its adhesive face, which microneedle is to be set on the double-faced adhesive tape.
Figure 14:
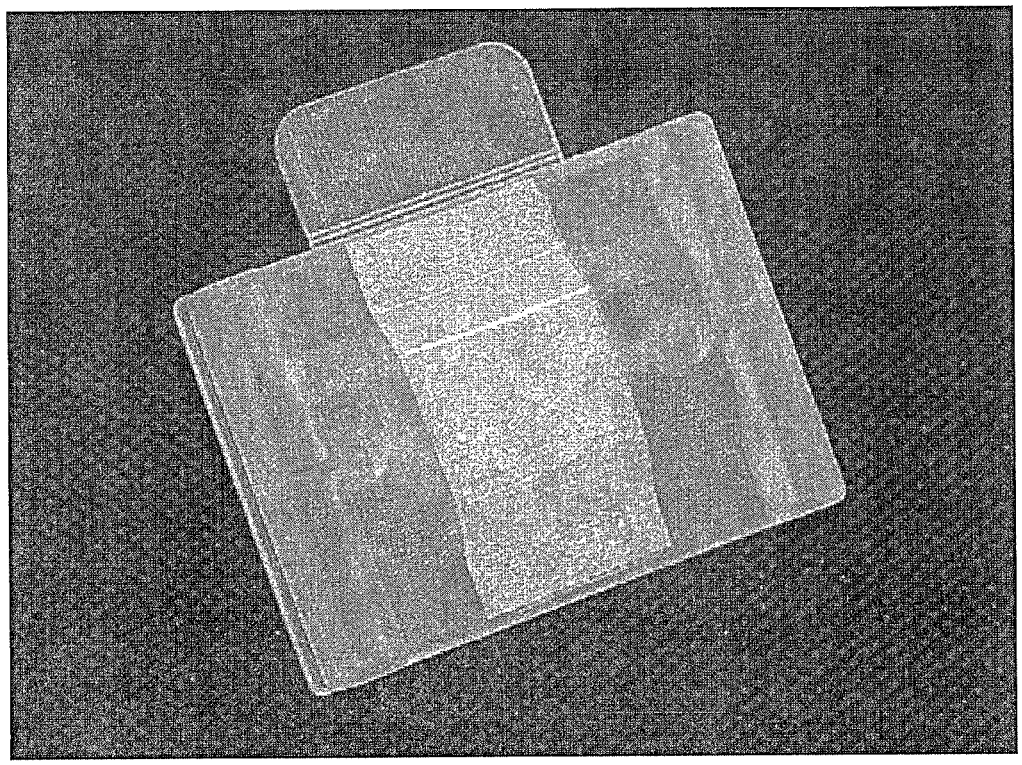
FIG. 14 is a perspective view (photograph) of the same Japanese "geta"-shaped applicator of the present invention as in FIG. 13 except that the assisting tool is different and the dip angle of the trapezoid profile (cross section) is 145°, which is formed by integral molding with a resin.

The "assisting tool" in the present invention refers to a supporting base for a microneedle to be placed in the applicators of FIG. 1 and FIG. 3. The assisting tool may be integrally molded with the applicator, as shown in FIG. 13 and FIG. 14. The shape of the assisting tool may be cylindrical, prismatic, polygonal columnar, circular truncated cone-shape, polygonal truncated pyramid-shape, or ingot-shape (roof-shape). Preferred is ingot-shape. The assisting tool can have an upper planar surface, a lower planar surface, and two inclined planar surfaces, as shown, for example, in FIGS. 7 and 23. As the material of the assisting tool, a hard resin can be mentioned, and a material same as that of the hard resin flat plate can be used. The height of the assisting tool (supporting base for microneedle) affects the puncturability of the microneedle, as well as greatly affects the adhesion of a tape used to adhere a microneedle to the skin. A preferable height of the assisting tool of the present invention is 0.5-10 mm, more preferably 2-7 mm. The bottom side part of the assisting tool for placing may be the same as the peripheral part of the applicator. For example, as shown in FIG. 8, the outer circumference of the applicator and the bottom side part of the assisting tool may be overlapped in the case of an ingot-shape (roof-shape) assisting tool, and the like.

Figure 18:
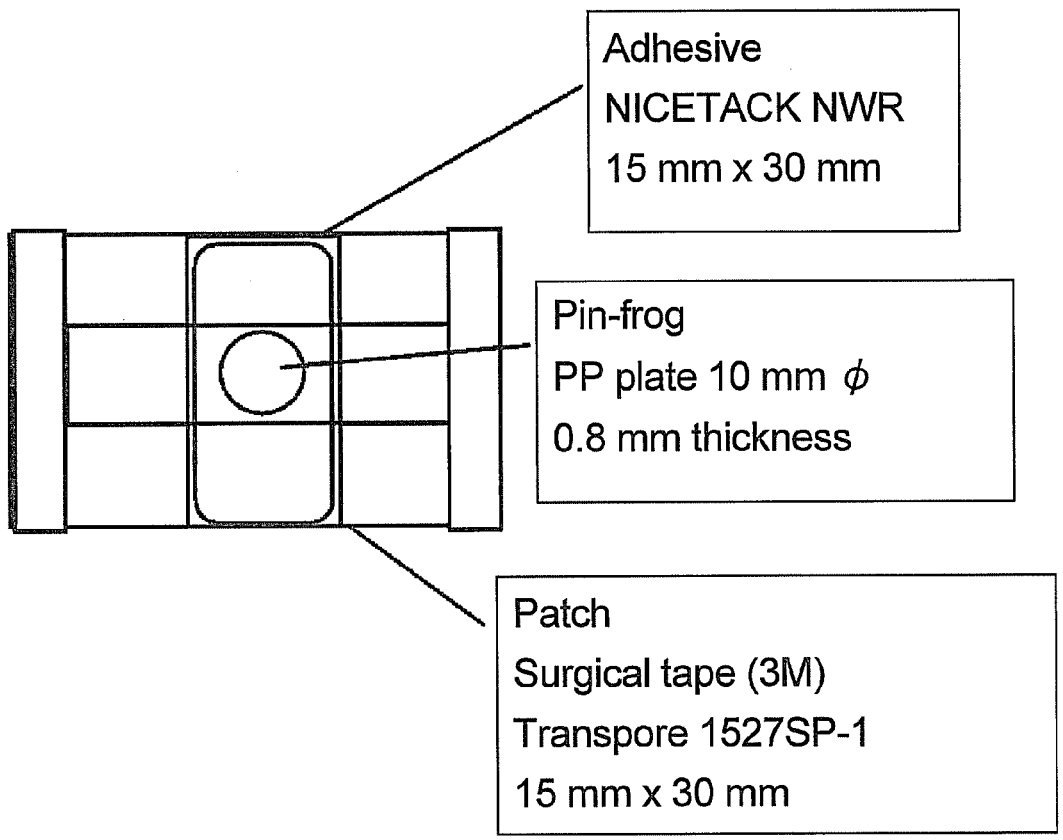
FIG. 18 is a schematic view of the applicator of the present invention wherein a microneedle (tape) is placed.

The "tape" in the present invention is a tape-like adhesion member to be placed on the assisting tool of the present invention with an adhesive such as a double-faced adhesive tape and the like. A microneedle is placed on an adhesive face of a tape placed on the horizontal part of the assisting tool, as shown in FIG. 18. As the applicator is pressed against the skin, the skin elevates to press against the assisting tool. As a result, the adhesive layer of the tape attaches to the skin and, when the force applied to the applicator is reduced, the tape is naturally peeled off at the both ends to closely adhere to the skin. As the tape in the present invention, a commercially available tape can be used, and is not particularly limited. For example, a surgical tape as the one shown in FIG. 18 can be used. As the shape of the tape, not only general shapes of the tape but also a circular tape as in FIG. 20 can be used. Even when a circular tape is used, it can be used as a rectangular strip tape, and can be closely adhered to the skin.

The "microneedle" in the present invention is a flat plate-shaped item having 10-500 small needles with a height of 100 μm-800 μm. Particularly in Experimental Examples 1 and 2, those of about 500 μm high were used. The thickness of the substrate of the microneedle may be 0.2-2 mm. The number of the microneedles is, for example, about 10×10. As the material of the microneedle, known materials can be used. For example, biodegradable resins such as aliphatic polyester resin (e.g., polylactic acid (PLA), polyglycolic acid (PGA), lactic acid glycolic acid copolymer and the like), polysaccharides (e.g., maltose, lactose, sucrose, mannitol, sorbitol and the like), and the like are preferably used. These microneedles can be appropriately produced by a known production method (e.g., WO2008/093679).

The "adhesive" in the present invention is used to adhere and hold the microneedle by adhesion, and simultaneously adhere the microneedle to the skin. In addition, a weaker adhesive is used to fix the tape to an assisting tool by adhesion. In this case, the relationship between an adhesive of the above-mentioned adhesive tape and the weaker adhesive to fix the tape is according to that described in Japanese Patent Application No. 2009-202328. As such adhesive, a widely-used known one can be appropriately selected and used. In addition, the strength/weakness can be adjusted according to the size of the adhesive area where an adhesive is used. For example, the adhesive is not particularly limited as long as it is a medical adhesive. Specific examples thereof include acrylic adhesives made of an acrylic polymer; styrene-diene-styrene block copolymer (e.g., a styrene-isoprene-styrene block copolymer, a styrene-butadiene-styrene block copolymer etc.); rubber adhesives such as polyisoprene, polyisobutylene, and polybutadiene; silicon adhesives such as silicon rubber, a dimethylsiloxane-based adhesive, and a diphenylsiloxane-based adhesive; vinyl ether adhesives such as polyvinyl methyl ether, polyvinyl ethyl ether, and polyvinyl isobutyl ether; vinyl ester adhesives such as a vinyl acetate-ethylene copolymer; and polyester adhesives made of a carboxylic component such as dimethyl terephthalate, dimethyl isophthalate, and dimethyl phthalate and a polyhydric alcohol component such as ethylene glycol. As for these adhesives, two or more kinds of them may be blended and used.

A drug may be applied to the microneedle used in the present invention. The drug to be applied is not particularly limited as long as it has been used for the treatment. When the drug is a biopolymer such as a protein, an antigen, an antibody, etc., it can be applied to the microneedle as an aqueous solution since its solubility in water is high. When the drug is a low molecular weight compound such as an antibiotic or an antipsychotic drug, it may be applied to the microneedle as an aqueous solution depending on its solubility, or may be applied thereto by the use of an organic solvent solution.

When a certain amount of drug is necessary to exhibit the effect, it is possible to allow small needles of the microneedle to support the necessary amount of drug by repeating the steps of immersing the small needles in an aqueous solution of the drug etc. and drying them.

The "side wall(s)" in the present invention is a member set on a peripheral part of the applicator of the present invention to fix the skin by pressing, as well as form a concave for housing a microneedle and an assisting tool. One embodiment thereof is a member forming the circular concave in the applicator shown in FIG. 4. Furthermore, a pair of prismatic members placed on both right-left ends of a rectangular resin flat plate as shown in FIG. 1 can be mentioned.

Figure 8:
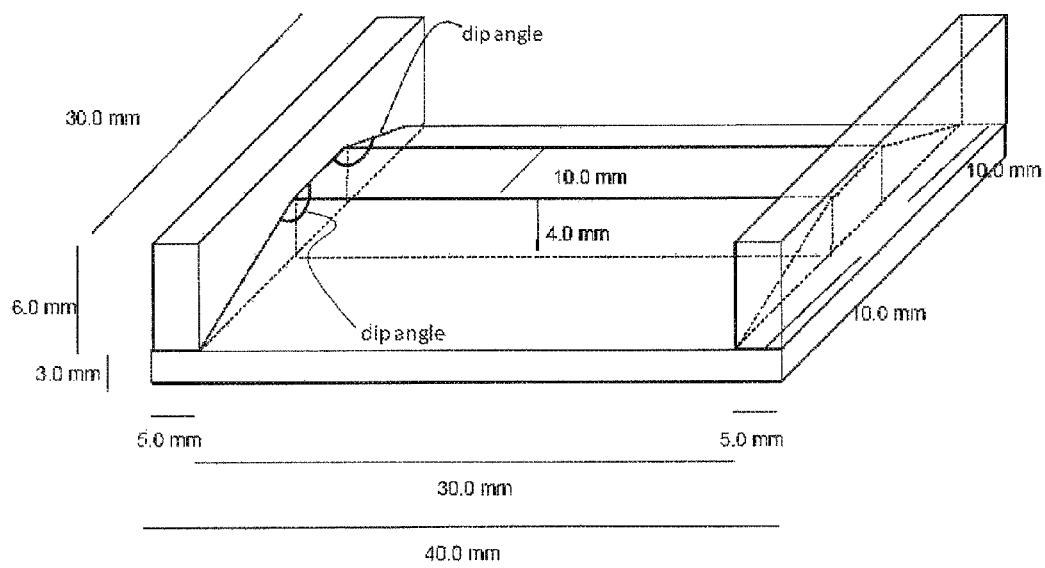
FIG. 8 is a perspective view of one embodiment of the Japanese "geta"-shaped applicator when the ingot-shape assisting tool of the present invention is set.
Figure 9:
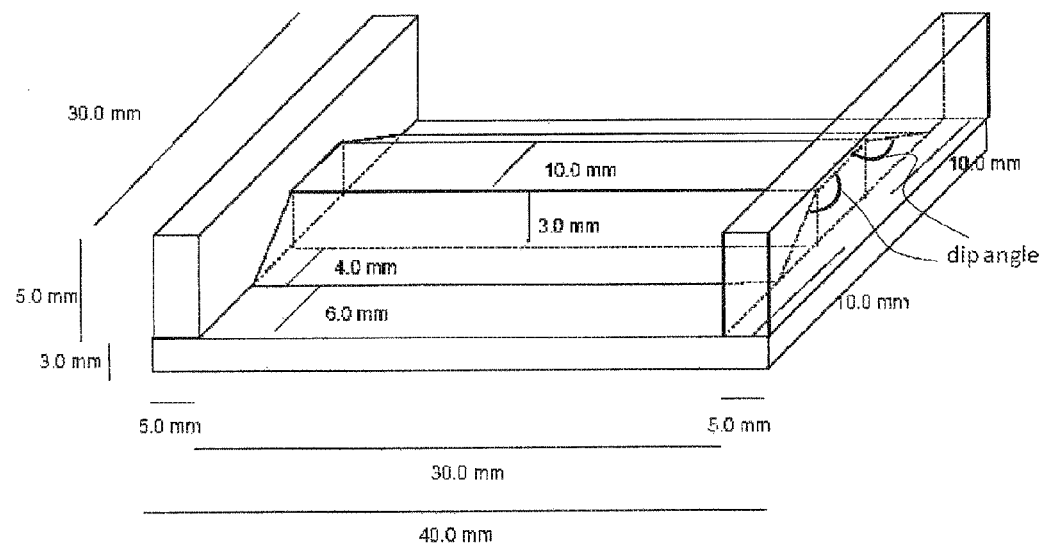
FIG. 9 is a perspective view of one embodiment of the Japanese "geta"-shaped applicator when the ingot-shape assisting tool (trapezoid dip angle 145° of the section) of the present invention is set.

The "side plates" in the present invention is a part of the above-mentioned "side wall(s)" and refers to, for example, a pair of prismatic members and plate members shown in FIG. 1, FIG. 8 and FIG. 9. The plate member may be a rectangle, or bent to partially form a circular arc.

The side wall(s) or side plates in the present invention may be integrally molded together with the assisting tool, as shown in FIG. 13 etc.

The "dip angle" in the present invention is an intersection angle formed by the upper line and the oblique line of the trapezoid shape which is a cross section of the ingot-shape (roof-shape). When the resin flat plate of the applicator has a constant size, as the assisting tool becomes higher, the dip angle of the present invention becomes smaller. The height of the assisting tool has a preferable range, and likewise, the dip angle is preferably 130-175° when used as a patch containing a microneedle. More preferable angle is 145-175°. When a microneedle is simply inserted, the height of the assisting tool also has a preferable range, and likewise, the dip angle is preferably 175° or below when used as a patch. More preferable angle is 90-175°.

Also, the trapezoid seen in the diameter section of a circular truncated cone and the central section of a polygonal pyramid also has a preferable range of angle as in the above.

Figure 23:
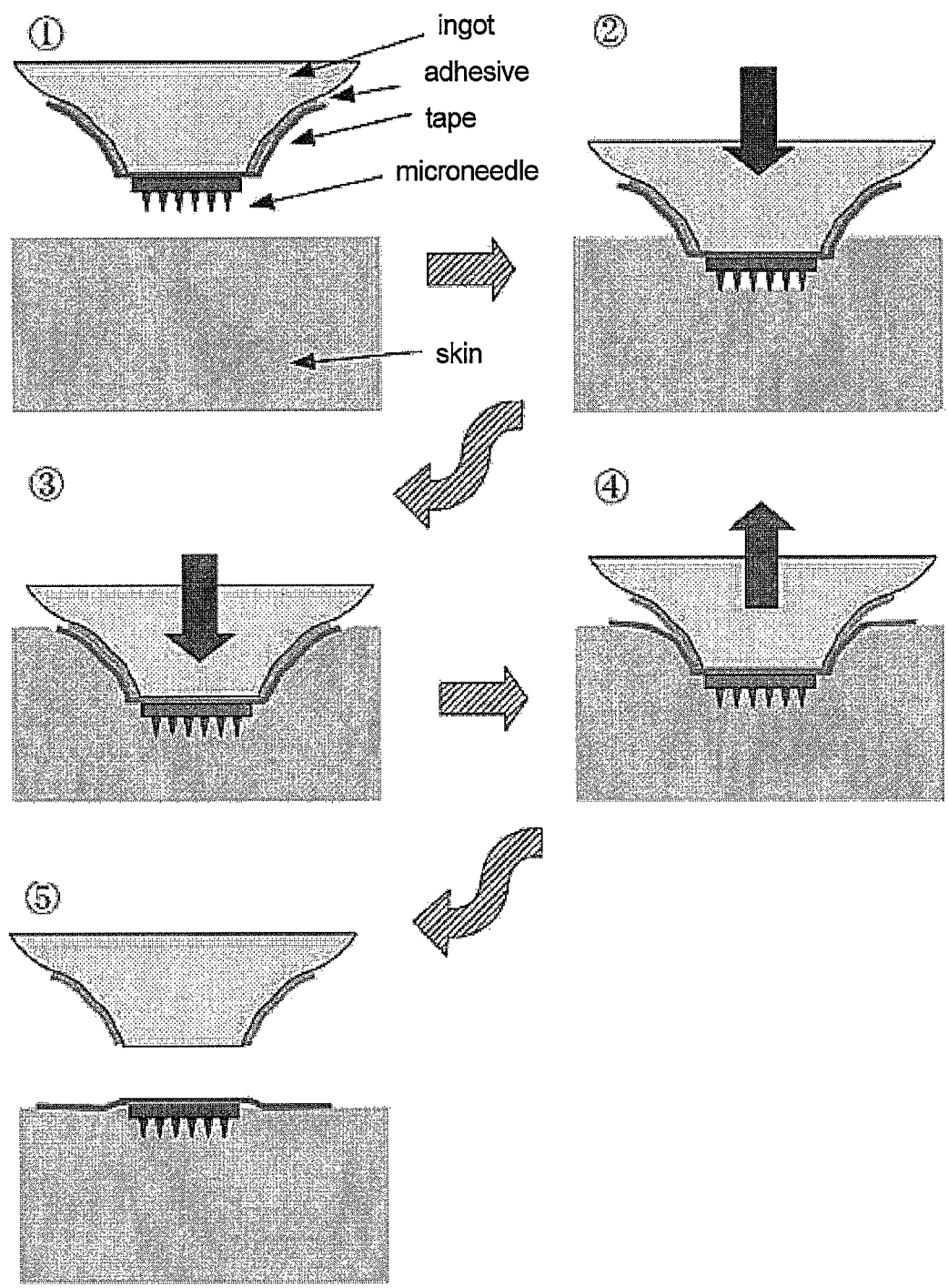
FIG. 23 shows conceptual diagrams of the process of adhering a patch containing the microneedle to the skin surface by using the applicator of the present invention. The applicator includes an assisting tool with an upper planar surface, a lower planar surface, and two inclined planar surfaces.

Different from the conventional flat plane applicators, the applicator containing the assisting tool of the present invention is preferable for puncturing the skin with a microneedle. To be precise, when a conventional flat plane applicator is used, the applicator and the tape are separated all at once upon release of the press of the applicator onto the skin, and the tape sometimes remains on the applicator. However, when the applicator of the present invention is used, as shown in FIG. 23, as the applicator is separated off from the skin upon release of the press onto the applicator, the tape peels off at the ends. Using the applicator of the present invention, the detachment stress of the applicator and the tape can be decreased, and therefore, when a patch carrying a microneedle is placed on the applicator, the applicator of the present invention can effectively keep the patch closely adhered to the skin.

In addition, an applicator containing the assisting tool of the present invention can determine the stress of the microneedle on the skin by determining the pressing range. For example, by marking the pressing range, the stress can be determined. When transferred from the applicator to the skin by the above-mentioned detachment of the tape, the detachment of the tape from the applicator does not occur unless the applicator is pressed for a certain range or more, and the tape is not transferred to the skin. That is, the pressing range can be set by the transfer of the tape to the skin, and the stress of the microneedle on the skin can also be set.

Therefore, the patch containing a microneedle set on the applicator of the present invention can be used to release a medicament (including a medicament having any pharmacological action) to the skin for an intradermal or topical treatment such as prophylactic vaccination. When the medicament to be used has a high molecular weight, a patch containing the microneedle of the present invention is useful. Examples of the medicament having a high molecular weight include protein, peptide, nucleotide sequence, monoclonal antibody, DNA vaccine, polysaccharide such as heparin, and antibody such as ceftriaxone.

Moreover, a patch containing the microneedle of the present invention enables transdermal absorption of a low molecular weight medicament difficult or impossible to be transdermally absorbed by other methods. Examples of the low molecular weight medicament include salt form; ion molecules such as bisphosphonate, preferably sodium alendronate or pamedronate and the like.

A patch containing the microneedle of the present invention can be used in the same manner as with other conventional patches. To enable more complete delivery of a medicament, adhesion for a long time is desirable. For example, 4 hr-1 week can be mentioned.

While the present invention includes some embodiments such as an applicator containing an assisting tool or an assisting tool, an applicator containing patch containing a microneedle or a microneedle, and the like, various kinds of applicators or applicators containing various microneedles can be used according to the present invention.

EXAMPLES

The present invention will be explained in more detail with reference to Examples and Experimental Examples; however, it is not limited to any of the following Examples and Experimental Examples.

(Experimental Example 1) Puncture Test of Pin-Frog-Shaped Microneedle to the Skin (1) Human Forearm Skin Model (A)

A 6 mm-thick sheet obtained by heat-melting SIS 30% and liquid paraffin 70% and molding the mixture was set, and a 9 mm-thick sheet obtained by heat-melting SIS 15% and liquid paraffin 85% and molding the mixture was laminated thereon to be 2 layers. On the substrate was placed the abdominal skin of a Wistar rat (male, 5 weeks) to give a human forearm skin model.

(2) Equipment

Using compact desktop type testing machine (Eztest) manufactured by Shimadzu Corporation, a plunger (φ5 mm) was set on the load cell thereof, and a φ12 mm polypropylene (PP) plate (0.8 mm thick) was further set on the tip thereof. A microneedle was placed on the tip of the PP plate.

(3) Pin-Frog-Shaped (Kenzan-Shaped) Microneedle

Using a resin sheet disk (circular plate) of polylactic acid (PLA) and polyglycolic acid (PGA) (φ10 mm, 2 mm thick), a pin-frog-shaped microneedle was prepared according to a known method (WO2008/093679 etc.).

(4) Evaluation Method

A plunger (φ5 mm) was set on the load cell of a compact desktop type testing machine (Eztest) manufactured by Shimadzu Corporation, and a φ12 mm PP plate (0.8 mm thick) was set on the tip thereof. A PGA microneedle (φ10 mm, 2 mm thick, 98 needles) was further placed on the tip of thereof. The tip of the microneedle was contacted with the skin surface of the above-mentioned human forearm skin model (A). The microneedle is pressed by the compact desktop type testing machine for a certain distance to cause puncture. The stress applied on the microneedle at that time was measured.

In addition, after puncture, the rat skin (Wister 5 w male abdomen) on the surface of the human forearm skin model (A) was taken out and stained with 1% gentian violet. Since the puncture sites are colored in purple, the number of colored sites was counted and the puncture rate of the microneedle was evaluated.

(5) Evaluation Results

The above-mentioned microneedle was pressed, and the stress at puncture and the puncture rate are shown in the following Table 1.

TABLE 1

| pressing distance (mm) | stress (N) | puncture rate (%) |
| --- | --- | --- |
| 4 | 1.5 | 30 |
| 5 | 2.1 | 40 |
| 6 | 2.9 | 50 |
| 7 | 3.6 | 60 |
| 8 | 4.7 | 100 |
| 10 | 6.3 | 100 |

As shown in the above-mentioned Table 1, it was found that the puncture rate and the stress on the microneedle are correlated. It was also found that the stress on the microneedle can be adjusted by the distance to be pressed.

To achieve 100% of the puncture rate, it was also found that the stress on the microneedle needs to be not less than 4N.

(Experimental Example 2) Skin Puncture Test by Applicator Holding Pin-Frog-Shaped Microneedle In the test of the above-mentioned Experimental Example 1, the microneedle was directly pressed against the skin model (A). From the previous findings, it is known that an applicator having a U-shaped cross-section as in FIG. 1 (a Japanese "geta"-shaped (a pair of side plates-shaped) applicator) provides a good puncture effect. Thus, changes in the puncturability of a pin-frog-shaped microneedle was examined by using such applicators (30×40 mm, various heights).

When the applicator shown in FIG. 1 is pressed against the skin, the skin free of pressing elevates perpendicularly. As a result, a microneedle can perpendicularly stick into the skin, affording very effective puncture.

Figure 2:
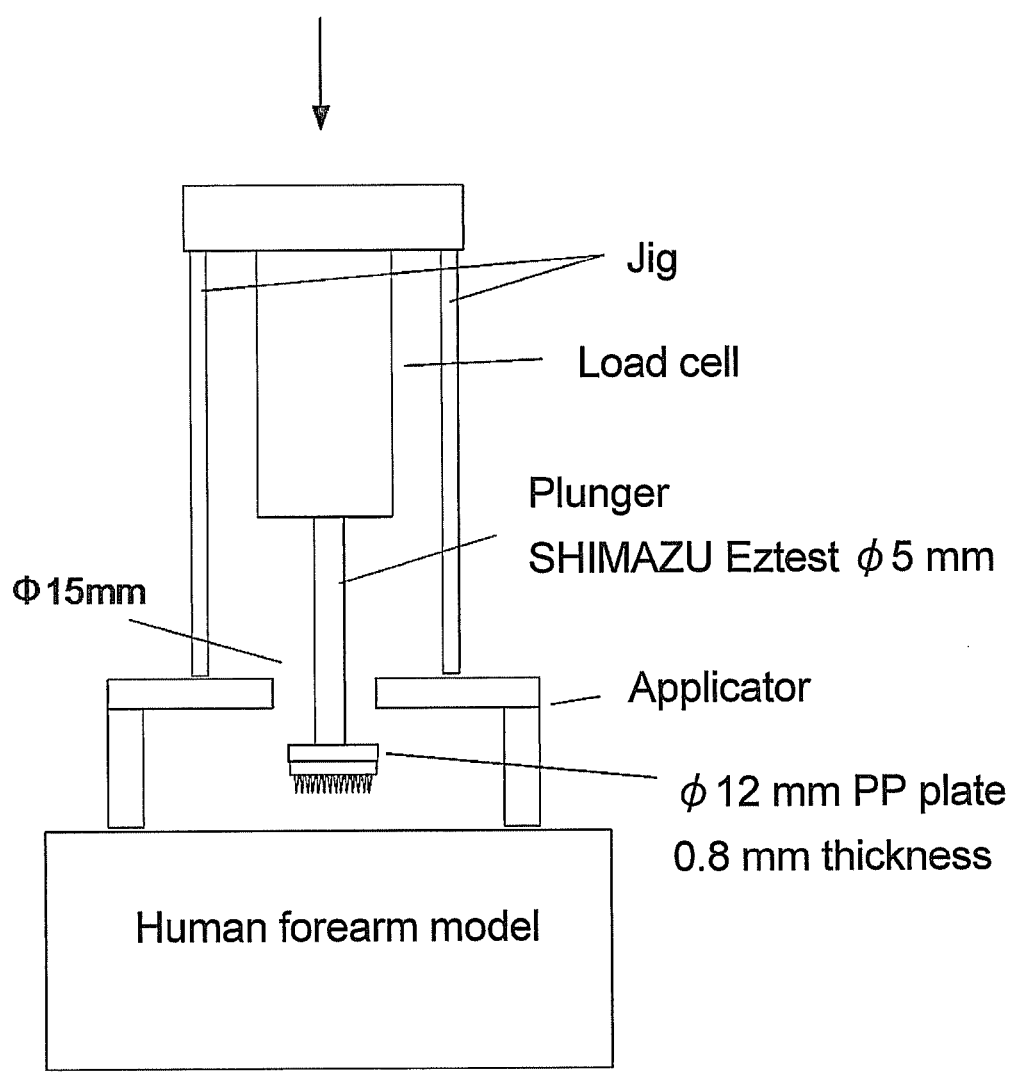
FIG. 2 is an outline of a test method to evaluate the stress applied to the microneedle and puncturability of the microneedle when the Japanese "geta"-shaped applicator of the present invention (FIG. 1) is used.

To evaluate puncturability of a microneedle by using an applicator, the jig shown in FIG. 2 was prepared and the measurement was performed. A plunger (φ5 mm) was set on the load cell of a compact desktop type testing machine (Eztest) manufactured by Shimadzu Corporation, and a φ12 mm PP plate (0.8 mm thick) was set on the tip thereof. A PGA pin-frog-shaped microneedle (φ10 mm, 2 mm thick, 98 needles) was further placed on the tip of thereof. To measure the stress on the tip of the needle of the pin-frog-shaped microneedle, the apparatus of FIG. 2 permitting synchronous pressing of the pin-frog-shaped microneedle and the applicator was set on the human forearm skin model (B). As the applicator, one free of an assisting tool was used. The apparatus of FIG. 2 was set such that the distance between the surface of the above-mentioned human forearm skin model (B) and the tip of the microneedle was about 0.5 mm or about 1.2 mm.

A force was applied on the jig of FIG. 2 in the compact desktop type testing machine to move the PGA pin-frog-shaped microneedle for a given distance to be pressed into the human forearm skin model (B), whereby the skin was punctured with the PGA pin-frog-shaped microneedle. The pressing distance and the stress during puncture were measured by the compact desktop type testing machine. After puncture, the rat skin (Wister 5 w male abdomen) on the surface of the human forearm skin model (B) was taken out and stained with 1% gentian violet. Since the puncture sites are colored in purple, the number of colored sites was counted and the puncture rate of the microneedle was evaluated.

(1) Human Forearm Skin Model (B)

A 19 mm-thick sheet obtained by heat-melting SIS 15% and liquid paraffin 85% and molding the mixture was set on a melamine resin flat plate, and a 3 mm-thick sheet obtained from the same materials was laminated thereon. A 0.49 mm-thick sheet of 100% SIS was laminated thereon to give 3 layers. On the substrate was placed the abdominal skin of a Wistar rat (male, 5 weeks) to give a human forearm skin model. This was used as human forearm skin model (B).

(2) Evaluation Results

The results of puncture with the above-mentioned PGA microneedle (98 needles) are shown in the following Table 2 and FIG. 3.

TABLE 2

| pressing distance (mm) | distance between model surface and microneedle tip | | | |
|---|---|---|---|---|
| | 0.5 mm | | 1.2 mm | |
| | stress (N) | puncture rate (%) | stress (N) | puncture rate (%) |
| 6 | 1.7 | 35 | | |
| 8 | 3.3 | 45 | 2.2 | 40 |
| 9 | 3.7 | 70 | 3.5 | 50 |
| 10 | 4.2 | 100 | | |

As shown in the above-mentioned Table 1 and Table 2, when the pressing distance of the pin-frog-shaped microneedle under the skin surface is the same, the stress applied to the microneedle was almost the same. When a stress of 4N or above is applied to the microneedle, the puncture rate was 100%.

As mentioned above, it has been clarified that, irrespective of the use or non-use of the applicator, the distance of the microneedle to be pressed into the skin determines the stress applied to the microneedle and the puncture rate.

Thus, a microneedle having needles with a somewhat blunt tip was used instead of the pin-frog-shaped microneedle used so far, and the puncturability thereof was evaluated. The results are shown in the following Table 3.

TABLE 3

| pressing | | puncture rate (%) | |
|---|---|---|---|
| distance (mm) | stress (N) | needle of Example 1 | somewhat blunt needle |
| 10 | 6.3 | 100 | 40 |

From the results of the above-mentioned Table 3, it has been clarified that the skin can be efficiently punctured with a smaller stress (smaller pressing distance into the skin) as the needle tip of a microneedle becomes sharper.

(Experimental Example 3) Evaluation Test of Stress Applied to Microneedle

Experimental Examples 1 and 2 showed that the puncturability of a microneedle is influenced by the strength of the stress applied to the microneedle (pressing distance into the skin). Thus, the difference in the stress due to the difference in the shape of the applicator was evaluated using the same pressing distance.

As an evaluation method, the following human forearm skin model (C) and the jig of FIG. 2 were used. However, a φ12 mm PP plate (0.8 mm thick) was set instead of the microneedle and the distance from the surface of the skin model was adjusted to 1.0 mm.

A) Verification of Evaluation Test Method (1) Human Forearm Skin Model (C)

A 19 mm-thick sheet obtained by heat-melting SIS 15% and liquid paraffin 85% and molding the mixture was set on a melamine resin flat plate, and a 3 mm-thick sheet obtained from the same materials was laid thereon. A 0.49 mm-thick sheet of 100% SIS was laid thereon to give 3 layers. This was used as human forearm skin model (C).

(2) Equipment

Using a compact desktop type testing machine (Eztest) manufactured by Shimadzu Corporation, a plunger (φ5 mm) was set on the load cell thereof, and two φ12 mm PP plates (0.8 mm thick) were further placed on the tip thereof.

(3) Evaluation Method

The above-mentioned jig and the above-mentioned compact desktop type testing machine were set on the above-mentioned human forearm skin model (C) as shown in FIG. 2. The applicator was pressed into the above-mentioned human forearm skin model (B) with the above-mentioned compact desktop type testing machine, and the stress was measured.

(4) Evaluation Results

The stress applied on the dummy PP plate of the above-mentioned microneedle was as shown in the following Table 4.

TABLE 4

| pressing distance (mm) | distance between model surface and microneedle tip | | |
|---|---|---|---|
| | 1.2 mm (Experimental Example 2) stress (N) | 1.0 mm (dummy) stress (N) | 0.5 mm (Experimental Example 2) stress (N) |
| 6 | | 2.2 | 1.7 |
| 8 | 2.2 | 3.5 | 3.3 |
| 9 | 3.5 | 4 | 3.7 |
| 10 | | 5.1 | 4.2 |

As shown in the above-mentioned Table 4, it has been found that a stress proportional to the pressing distance is applied even when the jig of FIG. 2, human forearm skin model (C) and a microneedle (dummy) were used. In addition, it has been shown that the difference of the microneedle and the dummy does not results in a large difference in the stress. Therefore, it has been considered that pressing the tip of the microneedle by 10 mm into the skin surface will achieve the puncture rate of 100%, since the stress of not less than 4N applies to the tip of the microneedle.

From the foregoing, it has been clarified that human forearm skin model (C) and the microneedle (dummy) can be sufficiently used as a model evaluation system for evaluating the puncturability of a microneedle. Therefore, using the present evaluation system, change of the stress on the microneedle caused by the shape of the applicator was evaluated (influence on puncturability).

B) Change of Stress on Microneedle Caused by Structure of Applicator (Influence on Puncturability of Microneedle (1) Selection of Applicator In the above-mentioned A), a Japanese "geta"-shaped applicator for pressing 2 points on the skin was used. Thus, the wappen-shaped applicator of FIG. 4 (30×30 mm, concave part φ25 mm) having an outer circumference wall was produced.

(2) Evaluation Method

A microneedle (dummy) was placed on the jig of FIG. 2 used in the above A) and pressed into the human forearm skin model (C) in the same manner as in the above A), and the pressing distance and stress were measured.

(3) Evaluation Results

The stress applied on the dummy PP plate of the above-mentioned microneedle was as shown in the following Table 5.

TABLE 5

| pressing distance (mm) | distance (1.0 mm) between model surface and microneedle tip | |
|---|---|---|
| | Japanese "geta"-shaped applicator (above A)) stress (N) | wappen-shaped applicator stress (N) |
| 6 | 2.2 | 1.4 |
| 8 | 3.5 | 2.3 |
| 9 | 4 | |
| 10 | 5.1 | 3.4 |
| 11 | | 4.0 |
| 12 | | 4.7 |

As shown in the above-mentioned Table 5, when the pressing distance was the same, the Japanese "geta"-shaped applicator showed a stronger stress (puncturability of microneedle is good when Japanese "geta"-shaped wappen is used), and the wappen-shaped applicator showed a weaker stress. This is considered to be attributable to the lower elevation of the skin when the wappen-shaped applicator is pressed into the skin than the Japanese "geta"-shaped applicator, since all periphery of the concave in the wappen-shaped applicator is surrounded.

Figure 5:
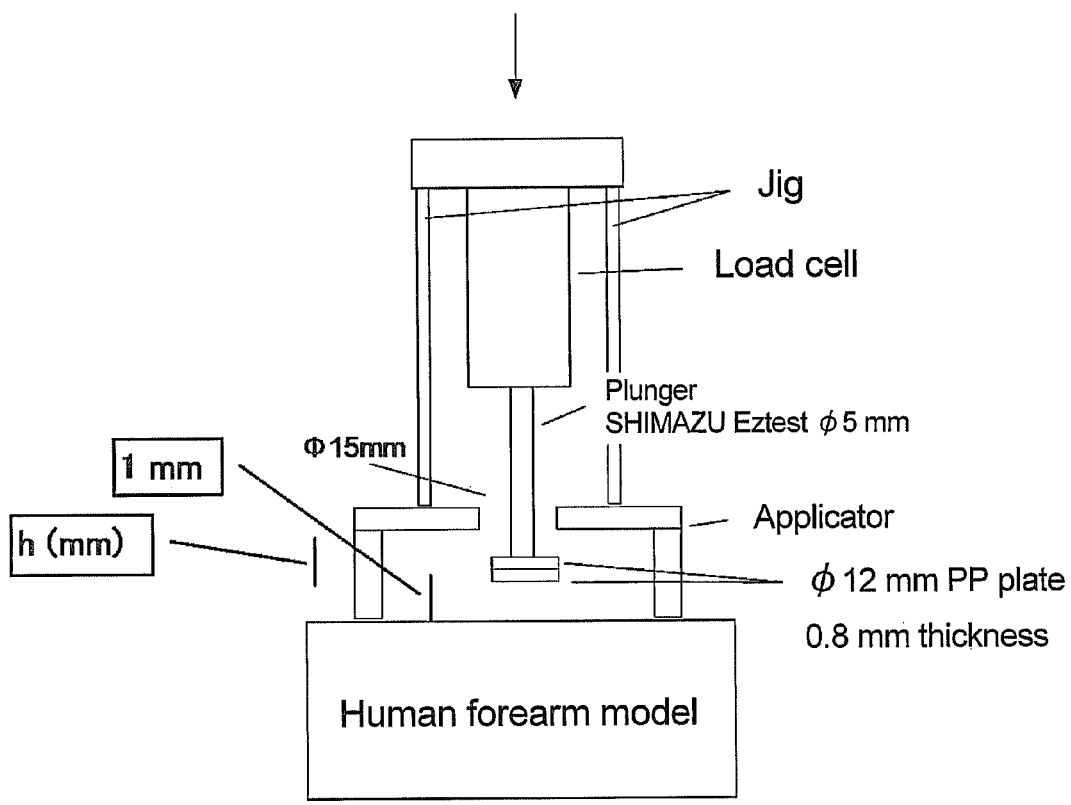
FIG. 5 is a schematic view of a test method to evaluate the relationship between the height of the assisting tool and the stress applied to the microneedle (dummy) in the Japanese "geta"-shaped applicator of the present invention.

(Experimental Example 4) Position of Supporting Base for Microneedle Placed in Applicator and Change of Stress on Microneedle As shown in the above-mentioned Experimental Example 3, the Japanese "geta"-shaped applicator elevates the skin surface more easily by pressing, which facilitates the microneedle to be pressed into the skin surface easily and deeply. In addition, protrusion of a supporting base (assisting tool) for microneedle in the Japanese "geta"-shaped applicator was considered to further facilitate the microneedle to be pressed into the skin surface when the skin elevates by pressing the applicator, thus increasing the stress applied to the microneedle. Thus, the jig of FIG. 5 was produced, and the relationship between the height of the supporting base (assisting tool) for the microneedle and the stress was evaluated. The distance of the skin surface and the tip of the microneedle was set to 1 mm as in Experimental Example 3. In FIG. 5, h shows the distance from the tip of the microneedle to the bottom face of the applicator. When the length of the microneedle is about 0.5 mm and the thickness of the substrate is 1 mm, the height of the assisting tool is shown by h−1.5 mm. The results are shown in the following Table 6.

TABLE 6

| pressing distance (mm) | height of assisting tool: h-1.5 (mm) | | | | | |
|---|---|---|---|---|---|---|
| | h = 0 | h = 1 | h = 2 | h = 3 | h = 4 | h = 5 |
| 6 | 1.2 | 1.9 | 2.2 | 2.2 | 2.3 | 2.2 |
| 8 | 1.9 | 2.8 | 3.4 | 3.5 | 3.8 | 3.7 |
| 10 | 2.6 | 3.8 | 4.6 | 5.1 | 5.4 | 5.4 |

From the results of Table 6, it has been considered that, when the pressing distance is 10 mm, the tip of the microneedle needs to protrude by 3 mm or more from the bottom face of the applicator so as to achieve the stress of not less than 4N to be applied to the microneedle, and not less than 5.1N to the dummy microneedle of Experimental Example 3. Therefore, the height of the assisting tool has been found to be sufficient when it is not less than 1.5 mm. The puncture rate of the microneedle is considered to be 100% when a Japanese "geta"-shaped applicator having such height of the assisting tool can be produced.

(Experimental Example 5) Position of Microneedle (Height of Supporting Base) and Change of Stress on Microneedle From the results of Experimental Example 4, it has been shown that the stress is higher when the tip of the microneedle is protruding somewhat from the bottom face of the applicator, and the puncturability of the microneedle is high. Thus, the jig of FIG. 6 was produced, and the influence of the side wall(s) of the applicator was removed. Using the jig, the level of protrusion of the assisting tool, to be provided with a microneedle, from the bottom face of the applicator, which is necessary for achieving a preferable puncture rate, can be directly evaluated.

Figure 6:
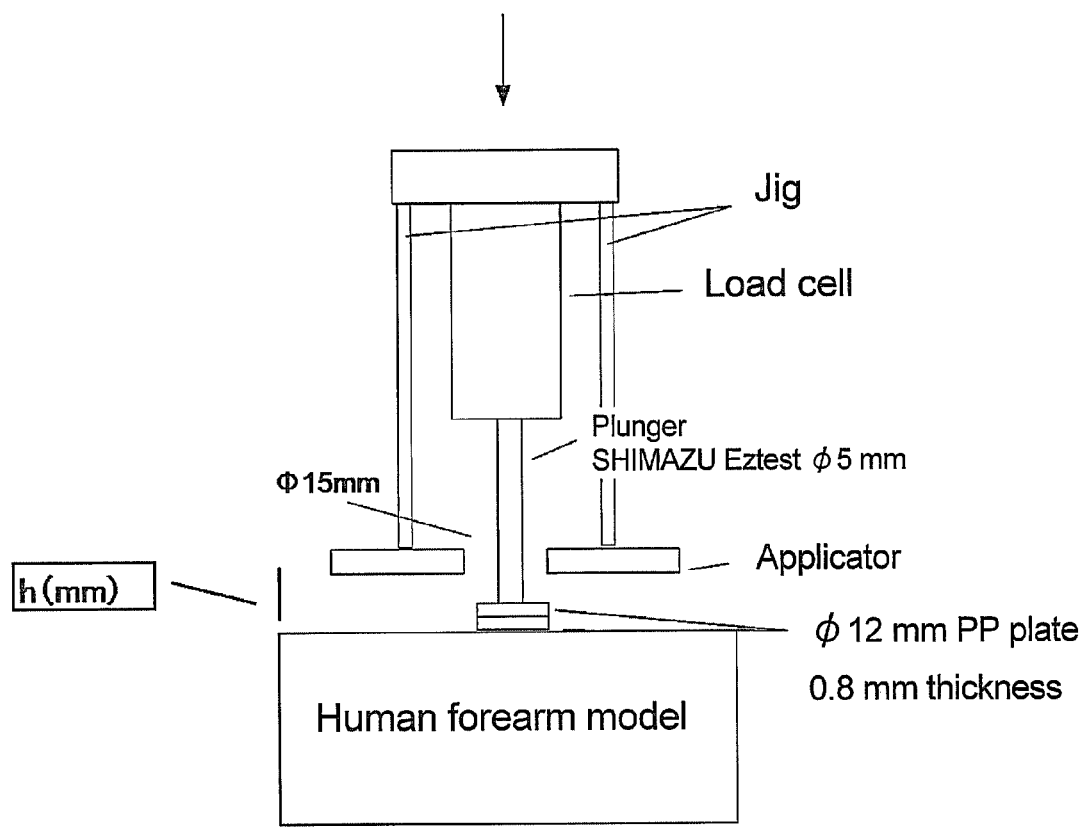
FIG. 6 is a schematic view of a test method to evaluate the relationship between the height of the assisting tool of the present invention (supporting base for microneedle) and the stress applied to the microneedle when the pressing distance of the applicator is changed.

Thus, the stress applied to the microneedle was evaluated by measurement using the jig of FIG. 6 and in the same manner as in Experimental Example 4. The height of the assisting tool can be shown by microneedle tip height (h)-1.5 mm, as in Experimental Example 4. The results are shown in the following Table 7.

TABLE 7

| pressing distance (mm) | height of assisting tool: h-1.5 mm | | | | | | |
|---|---|---|---|---|---|---|---|
| | h = 0 | h = 1 | h = 2 | h = 3 | h = 4 | h = 5 | h = 6 |
| 6 | 1.6 | 2.2 | 3.0 | 3.2 | 3.5 | 3.9 | 3.8 |
| 8 | 2.3 | 3.0 | 4.0 | 4.4 | 4.8 | 5.4 | 5.6 |
| 10 | 3.0 | 4.0 | 5.0 | 5.7 | 6.1 | 7.0 | 7.5 |
| 12 | 4.1 | | | | | | |

From the results of Table 7, it has been shown that protrusion of the tip of the microneedle from the bottom face of the applicator correspondingly facilitates application of a stress on the microneedle, and improves puncturability. It has been shown that, when the pressing distance is 10 mm, protrusion of the tip of the microneedle by about 2 mm sufficiently achieves a stress of 5N. In addition, when the assisting tool is higher, the stress applied on the microneedle of the applicator tends to increase even without pressing the applicator.

For example, it has been clarified that, when the assisting tool has a height of 3 mm, the stress of not less than about 5N can be applied to the microneedle (dummy) even when the applicator is pressed into the skin surface by 8 mm. That is, it has been shown that, when an assisting tool having a height of about 3 mm is placed in the applicator, the stress on the microneedle increases and the puncturability is improved more.

From the above findings, applicators having an assisting tool (supporting base) for a microneedle were produced in the following Examples 1-4, and the function thereof was evaluated.

(Example 1) Production of Applicator Containing Assisting Tool (Supporting Base for Microneedle)

An ingot-shape polypropylene assisting tool having a trapezoid cross-section (upper line length 10 mm, bottom line length 30 mm, trapezoid height 4 mm, intersection angle of upper line and oblique line 158°) and a length of 30 mm was produced.

Figure 7:
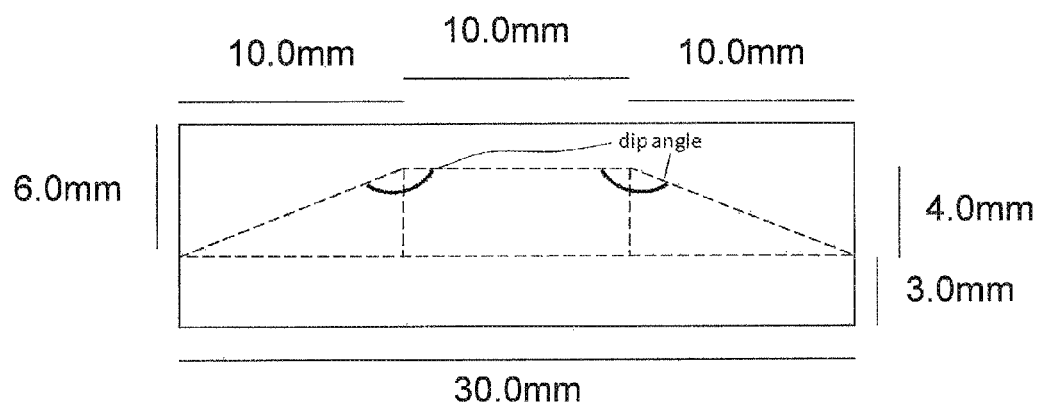
FIG. 7 is a side view of one embodiment of the Japanese "geta"-shaped applicator when the ingot-shape assisting tool of the present invention is set. The assisting tool has an upper planar surface, a lower planar surface, and two inclined planar surfaces.

A bottom plate (3×30×40 mm) and side plates (5×6×30 mm) were adhered with an adhesive to the above-mentioned assisting tool, as shown in FIG. 7. As a result, a polypropylene applicator incorporating the polypropylene assisting tool was produced, as shown in FIG. 8.

(Example 2) Production of Applicators Containing Various Sizes of Assisting Tools (1) Production of Assisting Tool (Supporting Base for Microneedle)

Ingot-shape polypropylene assisting tools having the same size (30×30 mm) as in Example 1 but different only in the height of sectional trapezoid were produced as shown in the following Table 8.

TABLE 8

| | height of trapezoid (mm) | | | | | | | |
|---|---|---|---|---|---|---|---|---|
| | 0 | 1.0 | 1.5 | 2.5 | 4.0 | 5.0 | 7.0 | 11.0 |
| intersection angle of upper line and side line | 180° | 175° | 172° | 166° | 158° | 153° | 145° | 132° |

Furthermore, ingot-shape polypropylene assisting tools having an upper line length 10 mm, and the same intersection angle of the upper line and the side line of 145°, but different heights of trapezoid cross-section (height 3 mm, 5 mm) were produced.

(2) Production of Various Applicators Incorporating the Above-Mentioned Assisting Tools a) The above-mentioned ingot-shape assisting tools described in Table 8 were cut in 30 mm length, and the applicators shown in the following Table 9 were produced in the same manner as in Example 1. The height of the side plates to be used was set to be always 2 mm longer than the height of the assisting tool. As a result, applicators having the same shape as the applicators of FIG. 8 and having different heights were produced.

TABLE 9

| | applicator No. | | | | | | | |
|---|---|---|---|---|---|---|---|---|
| | 1 | 2 | 3 | 4 | 5 | 6 | 7 | 8 |
| height (mm) of trapezoid | 0 | 1.0 | 1.5 | 2.5 | 4.0 | 5.0 | 7.0 | 11.0 |

TABLE 9-continued

| | applicator No. | | | | | | | |
|---|---|---|---|---|---|---|---|---|
| | 1 | 2 | 3 | 4 | 5 | 6 | 7 | 8 |
| intersection angle of upper line and side line | 180° | 175° | 172° | 166° | 158° | 153° | 145° | 132° |
| height of side plates | 2.0 | 3.0 | 3.5 | 4.5 | 6.0 | 7.0 | 9.0 | 13.0 | b) In the same manner as above and using the assisting tools of the above-mentioned Table 8, applicators having side plates having a height always 3 mm longer than the height of the assisting tool were produced as shown in the following Table 10.

TABLE 10

Figure 10:
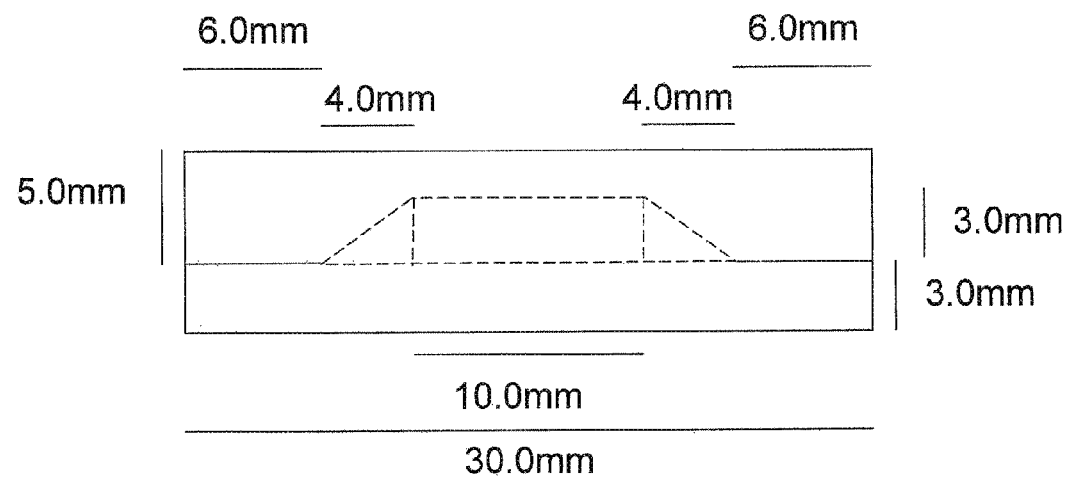
FIG. 10 is a side view of the Japanese "geta"-shaped applicator of FIG. 9.

| | applicator No. | | | | |
|---|---|---|---|---|---|
| | 9 | 10 | 11 | 12 | 13 |
| height (mm) of trapezoid | 1.5 | 2.5 | 4.0 | 5.0 | 7.0 |
| intersection angle of upper line and side line | 172° | 166° | 158° | 153° | 145° |
| height of side plates | 4.5 | 5.5 | 7.0 | 8.0 | 10.0 | c) An ingot-shape assisting tool having an upper line length 10 mm, the same intersection angle of the upper line and the side line of 145°, and the height of trapezoid section of 3 mm, 5 mm was cut in 30 mm length and the applicators shown in FIG. 9 were produced in the same manner as in Example 1. The applicators produced as a result are shown in the following Table 11. The side plates used had a height always 2 mm longer than the height of the assisting tool, as shown in FIG. 10.

TABLE 11

| | applicator No. | |
|---|---|---|
| | 14 | 15 |
| height (mm) of trapezoid | 3.0 | 5.0 |
| intersection angle of upper line and side line | 145° | 145° |
| height of side plates | 5.0 | 7.0 | d) An applicator wherein the assisting tools used in the above-mentioned applicator Nos. 2 and 4 were changed by 90 degrees was produced as shown in FIG. 11*b*). In the obtained applicator, the top of the ingot-shape assisting tool is parallel with the side plates. The height of the side plates to be used was set to be always 2 mm longer than the height of the assisting tool. The applicators produced as a result are shown in the following Table 12.

TABLE 12

Figure 12:
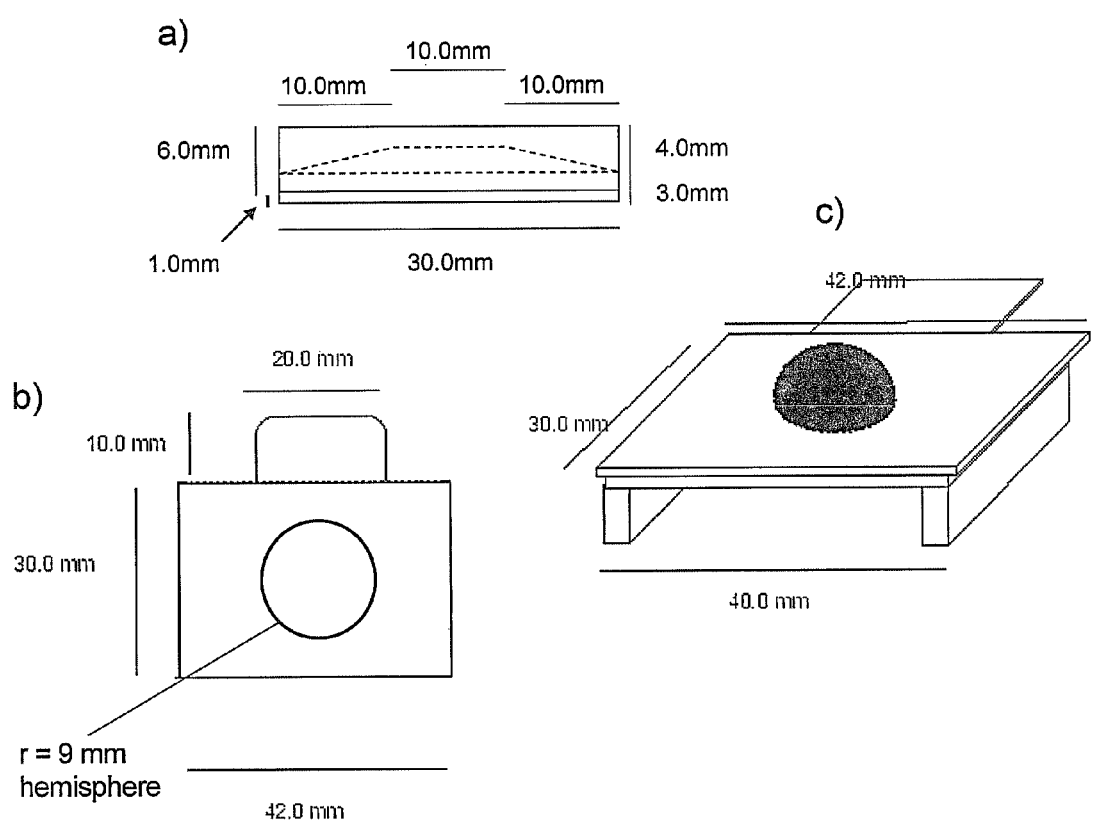
FIG. 12 shows a side view a) showing a resin plate placed to form a tag and a protrusion for easy grabbing of the Japanese "geta"-shaped applicator of the present invention, and a plane view b) and perspective view c) showing that a resin hemisphere protrusion for pressing is further set.
Figure 15:
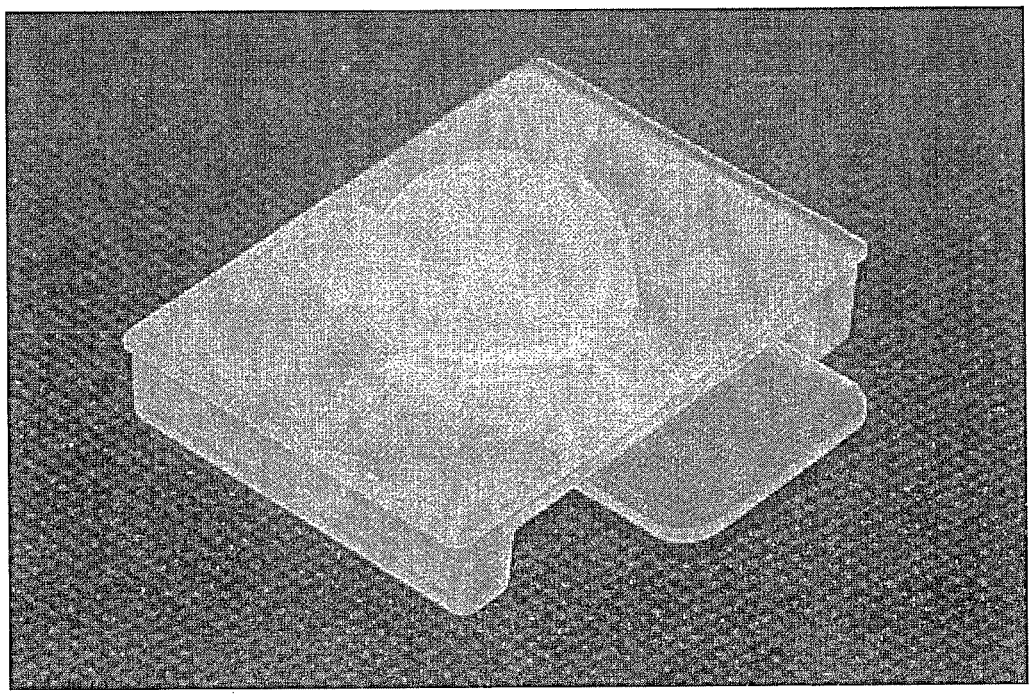
FIG. 15 is a perspective view (photograph) of the Japanese "geta"-shaped applicator of the present invention (FIG. 12b), c)), which is formed by integral molding with a resin.

| | applicator No. | |
|---|---|---|
| | 16 | 17 |
| height (mm) of trapezoid | 1.0 | 2.5 |
| intersection angle of upper line and side line | 175° | 166° |
| longitudinal length of side plate | 3.0 | 4.5 | e) A plate (1×30×42 mm) made of the same polypropylene material was adhered to the back face (surface opposite to assisting tool) of the above-mentioned applicator No. 5, and set such that the plate protruded by 1 mm from each of the side plates of the applicator, as shown in FIG. 12. In addition, a hemispherical convex (radius 9 mm) for pressing, which was made from the same material, was set in the center of the adhered polypropylene plate (1×30×42 mm). Furthermore, a 1 mm-thick resin plate and a resin hemisphere added to the side plates, back face and the assisting tool were integrally molded with a polypropylene resin to give the applicators described in FIG. 13, FIG. 15.

Figure 16:
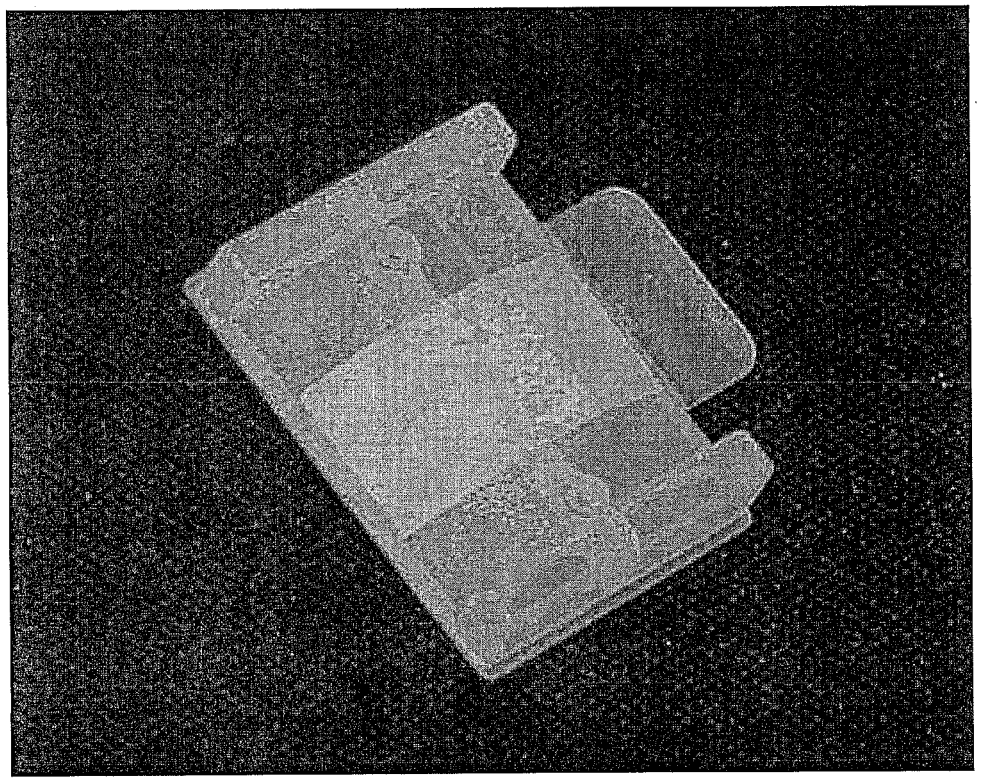
FIG. 16 is a perspective view (photograph) of one embodiment of the Japanese "geta"-shaped applicator of the present invention (FIG. 12a)), which is produced by integral molding of a resin.
Figure 17:
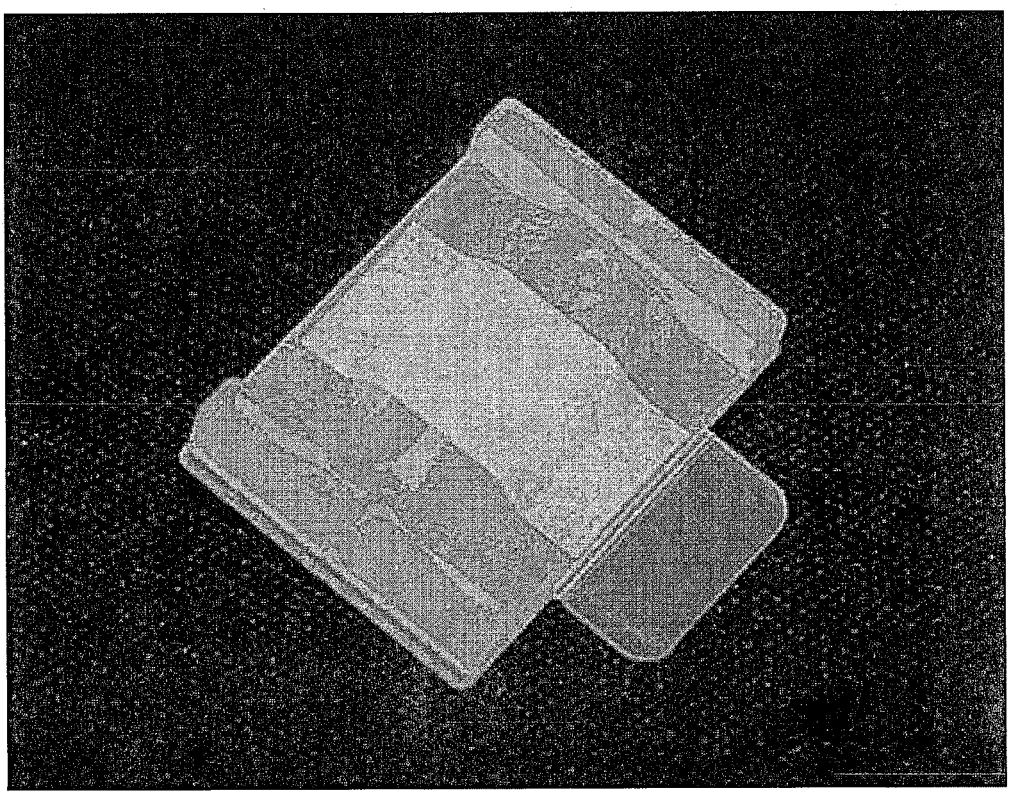
FIG. 17 is a perspective view (photograph) of one embodiment of the Japanese "geta"-shaped applicator of the present invention (FIG. 12a)), which is produced by integral molding of a resin, wherein the ingot-shape assisting tool of the present invention (trapezoid dip angle 145° of the section) is set.

Furthermore, using the applicator No. 14, an applicator of a shape added with a 1 mm-thick resin plate and a resin hemisphere, as shown in FIG. 12, was integrally molded with a polypropylene resin in the same manner as above to give the applicator described in FIG. 14.

f) Using the above-mentioned applicator Nos. 5 and 14, an applicator of a shape added with a 1 mm-thick resin plate but free of a resin hemisphere, as shown in FIG. 12, was integrally molded with a polypropylene resin in the same manner as in e). As a result, the applicators shown in FIG. 16, FIG. 17 were obtained.

By adding a convex for pressing, a force can be easily applied to the center when pressing the applicator, which increases the vertical travelling ability of the applicator. The shape of the convex for pressing is one permitting easy application of force on the center, and cylinder, prism, circular cone, pyramid, hemisphere and the like can be mentioned.

(Example 3) Production of Applicator Containing Pin-Frog-Shaped Microneedle (Tape Agent)

Figure 11:
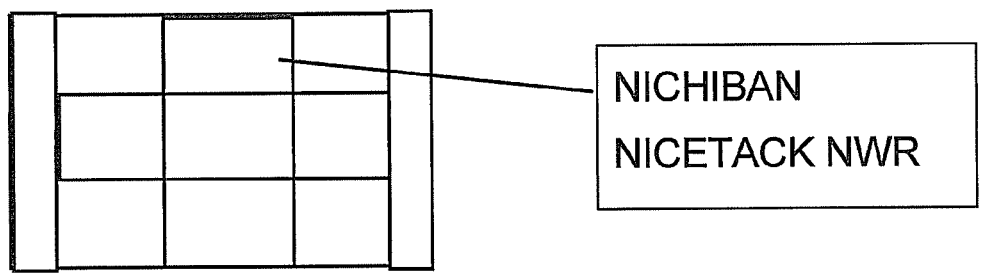
FIG. 11 are schematic views of the Japanese "geta"-shaped applicators (two kinds) of the present invention which show the state of the tapes placed alongside.
Figure 11:
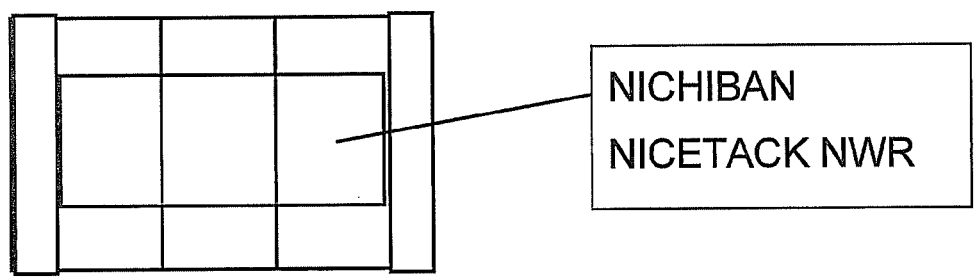

Using the applicators (No. 1-17) obtained in Example 2, a double-faced adhesive tape (NICETACK NWR manufactured by NICHIBAN, 15×30 mm) was adhered as shown in FIG. 11.

Figure 19:
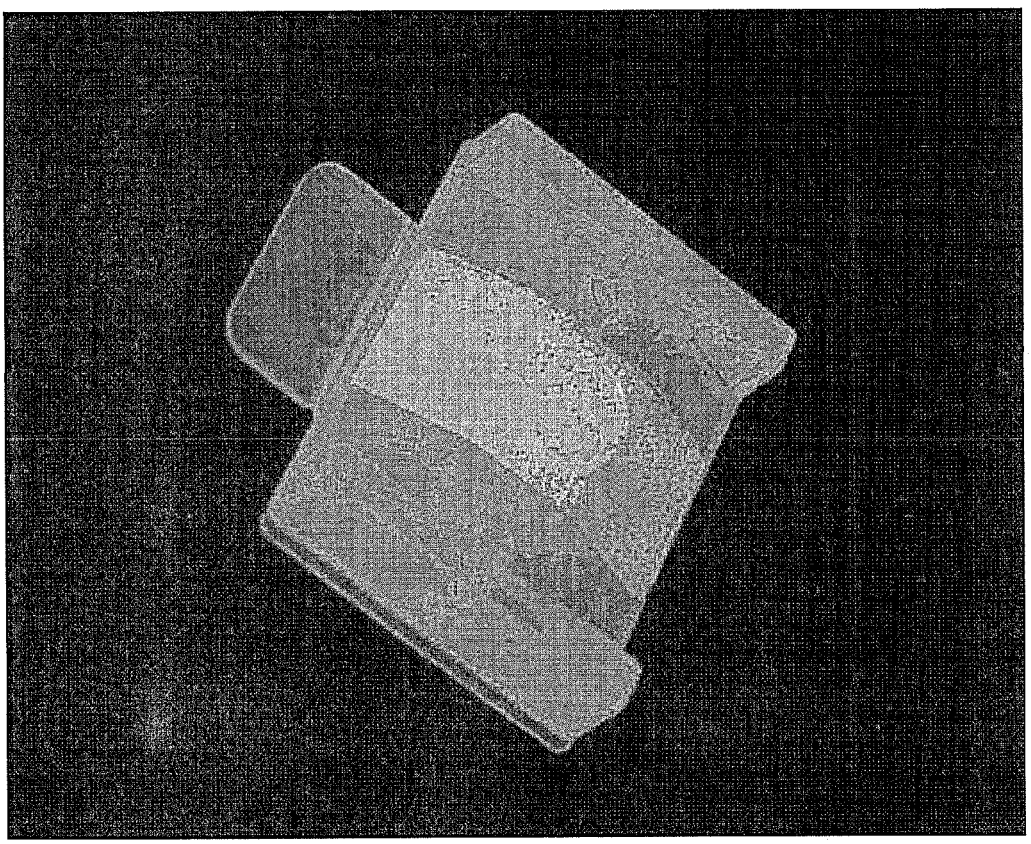
FIG. 19 is a perspective view (photograph) of the applicator of the present invention wherein a tape adhering the microneedle (dummy) of FIG. 13 is placed on the double-faced adhesive tape.

Furthermore, as shown in FIG. 18, the applicators were laid on the above-mentioned double-faced adhesive tape and adhered such that the adhesive face of the surgical tape (manufactured by 3M, Transpore 1527SP-1, 15×30 mm) became the surface. A pin-frog-shaped microneedle or a polypropylene plate as a dummy (diameter 12 mm, 0.8 thick) was set in the center of the adhesive face of the above-mentioned surgical tape (top of assisting tool). Alternatively, a polypropylene plate as a dummy was laid on the surgical tape as shown in FIG. 13, which was placed on the above-mentioned double-faced adhesive tape to give the applicator containing a pin-frog-shaped microneedle, as shown in FIG. 19.

(Example 4) Production of Applicator Containing Pin-Frog-Shaped Microneedle (Tape Agent)

Figure 20:
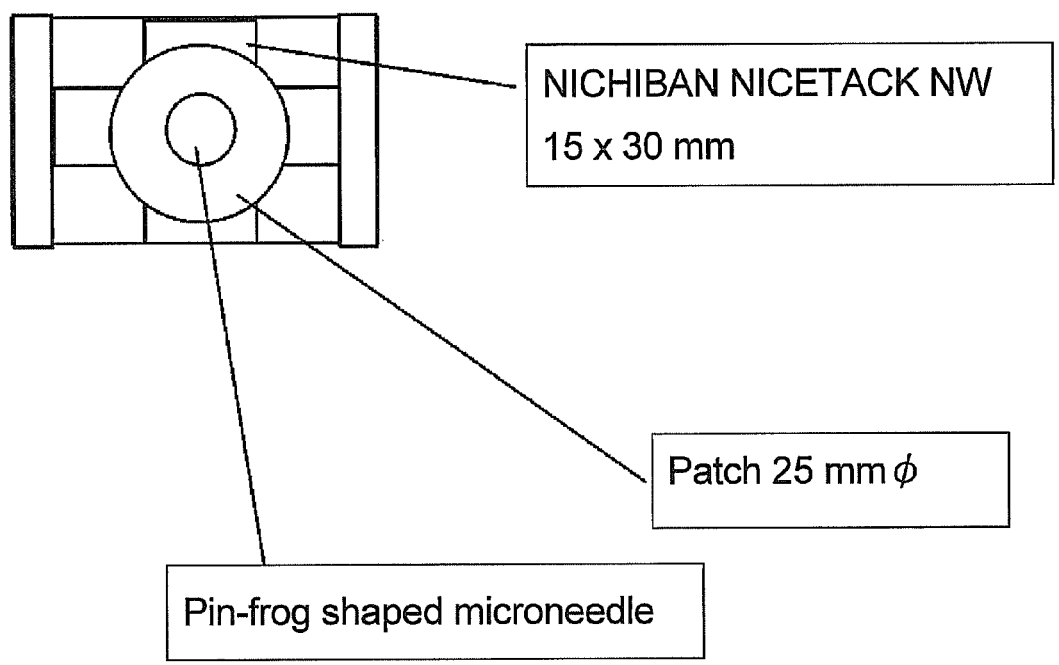
FIG. 20 is a schematic view of the applicator of the present invention wherein a microneedle (circular-shaped patch) is placed.

Using the applicator No. 5 obtained in Example 2, a double-faced adhesive tape (NICETACK NWR manufactured by NICHIBAN, 15×30 mm) was adhered as shown in FIG. 20.

Furthermore, a circular shape (Pore Tape MD-025-N (manufactured by Kyowa Limited, diameter 25 mm) was laid on the above-mentioned double-faced adhesive tape and adhered. A pin-frog-shaped microneedle or a polypropylene plate as a dummy (diameter 12 mm, 0.8 thick) was set in the center of the adhesive face of the above-mentioned surgical tape (top of assisting tool), whereby an applicator containing a pin-frog-shaped microneedle was produced.

(Experimental Example 6) Skin Contact Evaluation Test of Applicator Containing Assisting Tool When the applicators produced in Examples 3-4 are closely pressed against the skin, the microneedle punctures the skin, the adhesive face of the tape contacts and attaches to the skin. Then, the extent of pressing of the applicator necessary for adhering the tape to the skin together with the microneedle was examined. Whether the tape contacts and adheres to the skin is considered to be greatly affected by the pressing distance into the skin and the shape (angle) of the assisting tool in the applicator. Thus, the shape of the assisting tool was evaluated by the following method.

(1) Evaluation Test Method

The human forearm skin model (B) described in Experimental Example 3 was used.

(2) Applicator

Figure 21:
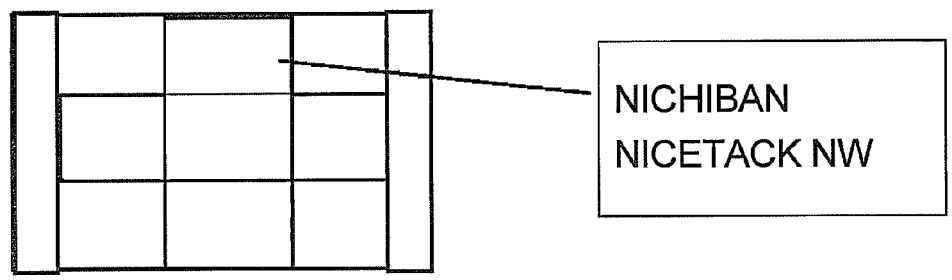
FIG. 21 shows schematic views of applicators for measuring the area of a tape agent to be attached to the skin by placing a tape on the Japanese "geta"-shaped applicator of the present invention and pressing against a skin model (distance) of ink adhering to the trapezoidal side surface of the assisting tool.
Figure 21:
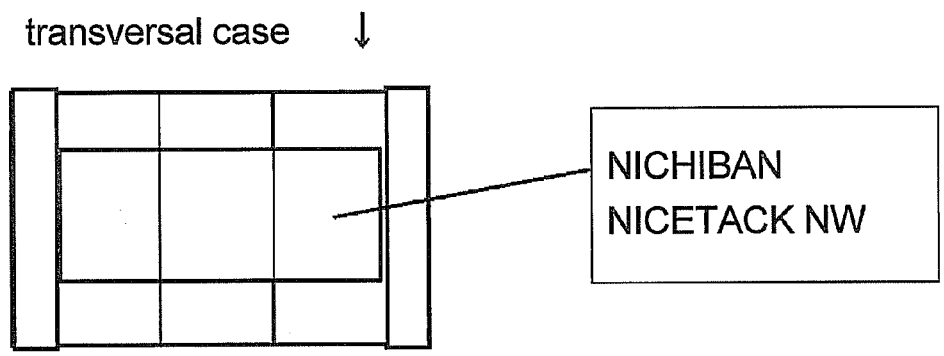

Using the applicator of Example 2, a double-faced adhesive tape (15×30 mm, NICETACK NW, manufactured by NICHIBAN) was adhered to the assisting tool as shown in FIG. 21.

(3) Equipment

Using a compact desktop type testing machine (Eztest) manufactured by Shimadzu Corporation, a plunger (φ5 mm) was set to the load cell thereof, and a φ12 mm PP plate (0.8 mm thick) was further set to the tip thereof.

(3) Evaluation Method

Figure 22:
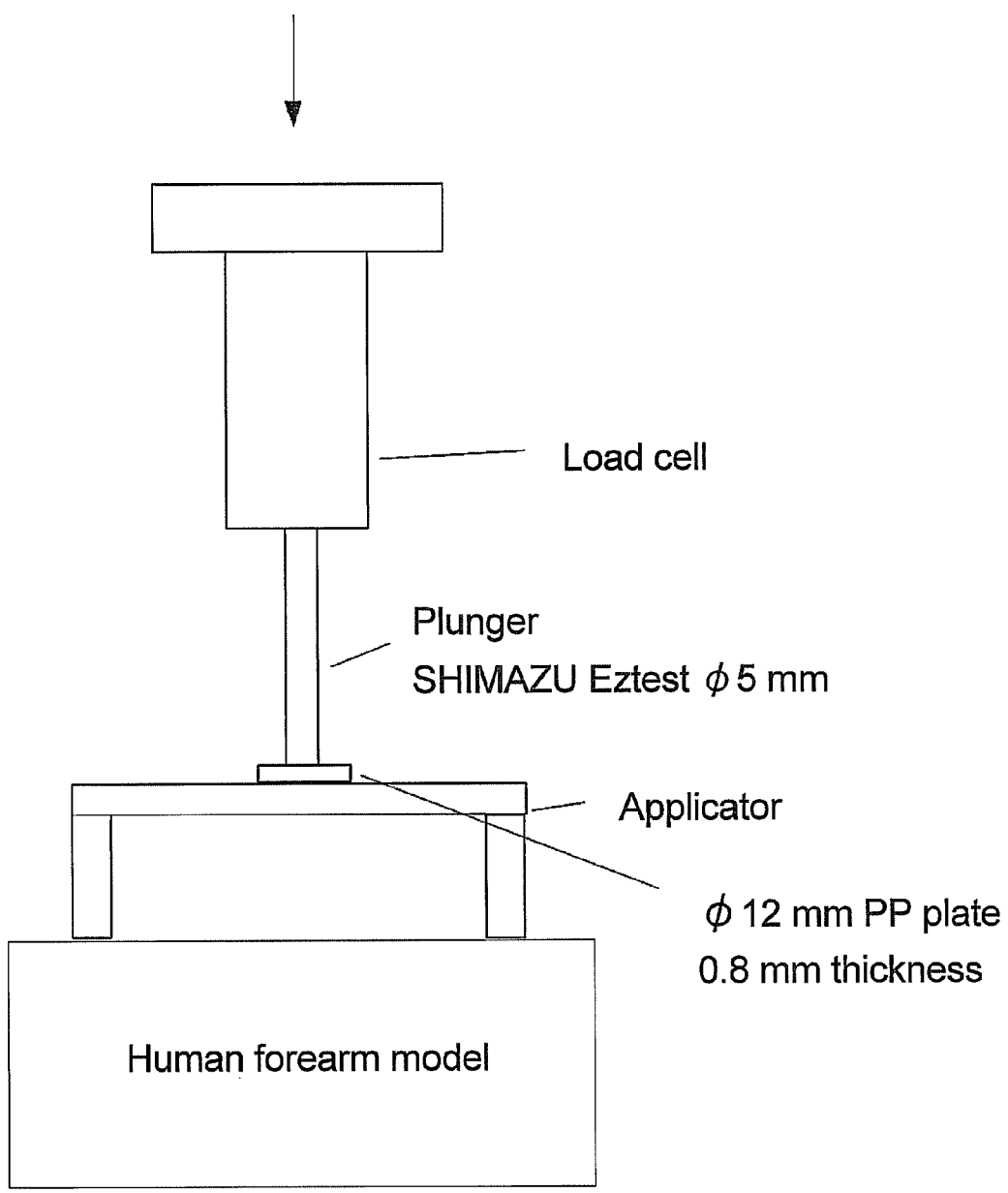
FIG. 22 is a schematic view of the test method for pressing the applicator of FIG. 21 against the skin model.

As the evaluation method, the method shown in FIG. 22 was used. First, oily ink (Mckee manufactured by ZEBRA) was applied to the above-mentioned human forearm skin model (B). Thereon were placed the above-mentioned applicator and the above-mentioned compact desktop type testing machine. The applicator was pressed by the above-mentioned compact desktop type testing machine into the above-mentioned human forearm skin model (B), and the area of the ink attached to the double-faced adhesive tape adhered to the applicator was measured.

(4) Evaluation Results a) Applicator Wherein the Top of Ingot-Shape Assisting Tool is Perpendicular to Side Plates:

As the applicator, the applicators shown in the following Table 13 were used to evaluate the relationship between the pressing distance into the skin model and the area of the ink attached to the tape. The area of ink attachment was evaluated by the ink attachment distance (mm) in the ingot-shape inclined plane of the assisting tool since the tape has the same width. The results of the inclined plane attachment distance (total of the left and right inclined planes) are shown below.

TABLE 13

| | applicator No. | | | | | | | |
|---|---|---|---|---|---|---|---|---|
| | 1 | 2 | 3 | 4 | 5 | 6 | 7 | 8 |
| pressing distance (mm) | 0 mm 180° | 1.0 mm 175° | 1.5 mm 172° | 2.5 mm 166° | 4.0 mm 158° | 5.0 mm 153° | 7.0 mm 145° | 11.0 mm 132° |
| 1 | 0 | 0 | 0 | 0 | 0 | 0 | 0 | 0 |
| 2 | 0 | 0 | 0 | 0 | 0 | 0 | 0 | 0 |
| 3 | 20 | 0 | 0 | 0 | 0 | 0 | 0 | 0 |
| 4 | | 0 | 0 | 0 | 0 | 0 | 0 | 0 |
| 5 | | 12 | 0 | 0 | 0 | 0 | 0 | 0 |

TABLE 13-continued

| | applicator No. | | | | | | | |
|---|---|---|---|---|---|---|---|---|
| | 1 | 2 | 3 | 4 | 5 | 6 | 7 | 8 |
| pressing distance (mm) | 0 mm 180° | 1.0 mm 175° | 1.5 mm 172° | 2.5 mm 166° | 4.0 mm 158° | 5.0 mm 153° | 7.0 mm 145° | 11.0 mm 132° |
| 6 | | 20 | 12 | 7 | 0 | 0 | 0 | 0 |
| 7 | | | 13 | 11 | 7 | 3 | 0 | 0 |
| 8 | | | 20 | 16 | 9 | 8 | 3 | 0 |
| 9 | | | | 20 | 13 | 10 | 7 | 0 |
| 10 | | | | 20 | 20 | 14 | 9 | 2 |
| 11 | | | | | | 20 | 13 | 6 |
| 12 | | | | | | | 17 | 10 |
| 13 | | | | | | | 20 | 12 |
| 14 | | | | | | | | |
| 15 | | | | | | | | 18 |
| 16 | | | | | | | | 20 |

[Note]
Since the length of the tape is 30 mm and the top part of the assisting tool is 10 mm, the length of the tape present in the left and right inclined planes is 10 mm for both left and right.

As shown in the above-mentioned Table 13, it has been clarified that, as the angle of the trapezoid section in the assisting tool becomes smaller and the height of the assisting tool becomes higher, the skin does not come into contact with the entirety of the tape unless the assisting tool is pressed deeper. It has been clarified that the pressing distance necessary for the entire tape to be in contact with the skin is about 5 mm higher than the height of the assisting tool in the applicator.

The pressing distance into the skin has an upper limit due to the thickness of the skin, and about 15 mm is considered to be appropriate. Therefore, an appropriate height of the assisting tool was considered to be not more than 10 mm.

Then, using a human forearm skin model (B) free of ink coating, the applicator was pressed in the same manner as above, and the time point when the double-faced adhesive tape is detached from the assisting tool and attached and adhered to the skin model was evaluated. The results are shown in the following Table 14.

TABLE 14

| | applicator No. | | | | | | | |
|---|---|---|---|---|---|---|---|---|
| | 1 | 2 | 3 | 4 | 5 | 6 | 7 | 8 |
| pressing distance (mm) | 0 mm 180° | 1.0 mm 175° | 1.5 mm 172° | 2.5 mm 166° | 4.0 mm 158° | 5.0 mm 153° | 7.0 mm 145° | 11.0 mm 132° |
| 1 | X | X | X | X | X | X | X | X |
| 2 | X | X | X | X | X | X | X | X |
| 3 | ○ | X | X | X | X | X | X | X |
| 4 | | X | X | X | X | X | X | X |
| 5 | | ○ | X | X | X | X | X | X |
| 6 | | ○ | ○ | X | X | X | X | X |
| 7 | | | ○ | ○ | X | X | X | X |
| 8 | | | ○ | ○ | X | X | X | X |
| 9 | | | | ○ | ○ | ○ | X | X |
| 10 | | | | ○ | ○ | ○ | ○ | X |
| 11 | | | | | ○ | ○ | ○ | X |
| 12 | | | | | | ○ | ○ | ○ |
| 13 | | | | | | | ○ | ○ |

[Note]
X: tape did not detach from the assisting tool.
○: tape detached and adhered to the skin model.

From the above tape detachment test, a new effect of the ingot-shape of assisting tool of the present invention could be found. That is, when the applicator is pressed against the skin to allow close adhesion of the skin to the assisting tool, and the pressing is lifted, the applicator is pushed back from the skin. In this event, the tape attached to the skin starts to peel from the end of the double-faced adhesive tape due to the inclined plane of the assisting tool. As a result, the tape could be closely and finely adhered to the skin without lifting during the adhesion process.

The same effect as mentioned above could be obtained with a tape containing a microneedle, and further, irrespective of the shape of the tape, the circular tape containing a microneedle as in FIG. 19 could also be finely adhered to the skin.

As shown in the above-mentioned Table 14, for a tape placed in the applicator to be adhered to the skin, not less than 50% of the entire tape needs to be attached to the skin irrespective of the presence or absence of a microneedle.

From the results of Table 7, for sufficient puncture of a microneedle into the skin, 5N stress needs to be applied to the tip of the microneedle. For this to be achieved, the height of the assisting tool is desirably at least 0.5 mm and, from the results of Table 13, the height of the assisting tool is desirably not more than 10 mm. Furthermore, it has been clarified that, in consideration of the adhesion of the tape to the skin, when the applicator is pressed until the stress (5N) necessary for a microneedle to be sufficiently punctured into the skin is applied, the tape is finely adhered to the skin by pressing the applicator against the skin and lifting the pressing, since the both ends of the tape peel from the assisting tool to allow adhesion. In the applicators used in Table 14, the difference between the height of the side plates and the height of the assisting tool is 2 mm. Therefore, when an applicator wherein the difference between the height of the side plates and the height of the assisting tool is 3 mm is separately used, the distance of about 1 mm needs to be further pressed into the skin.

Then, using applicators (Nos. 14, 15) wherein a dip angle of an assisting tool (angle of intersection of upper line and side line) is constantly 145° and the height of the trapezoid is different, the contact area of the assisting tool to the skin was evaluated in the same manner as above. The results are shown in the following Table 15.

TABLE 15

| | applicator No. | | |
|---|---|---|---|
| | 14 | 15 | 7 |
| | height (mm) of trapezoid | | |
| pressing distance | 3.0 | 5.0 | 7.0 |
| | angle of intersection of upper line and side line | | |
| (mm) | 145° | 145° | 145° |
| 1 | 0 | 0 | 0 |
| 2 | 0 | 0 | 0 |
| 3 | 0 | 0 | 0 |
| 4 | 0 | 0 | 0 |
| 5 | 0 | 0 | 0 |
| 6 | 0 | 0 | 0 |
| 7 | 0 | 0 | 0 |
| 8 | 2 | 3 | 3 |
| 9 | 10 | 6 | 7 |
| 10 | 12 | 8 | 9 |
| 11 | 16 | 11 | 13 |
| 12 | | 12 | 17 |
| 13 | | 13 | 20 |
| 14 | | | |
| 15 | 18 | 14 | |
| 16 | | | |

As shown in the above-mentioned Table 15, it has been clarified that, when the angle of the trapezoid section in the assisting tool is the same (145°), the skin does not sufficiently contact with the entire tape even when the assisting tool is deeply pressed. On the other hand, it has been known that, for the applicator No. 7, the skin comes into contact with the tape in proportion to the pressing distance. Thus, it has been shown that the contact area between the tape and the skin varies depending on the shape of the trapezoid part.

Then, using a human forearm skin model (C) free of ink coating, the applicator was pressed in the same manner as above, and the time point when the double-faced adhesive tape is detached from the assisting tool and attached and adhered to the skin model was evaluated. The results are shown in the following Table 16.

TABLE 16

| pressing distance (mm) | applicator No. | | |
|---|---|---|---|
| | 14 3.0 mm 145° | 15 5.0 mm 145° | 7 7.0 mm 145° |
| 1 | X | X | X |
| 2 | X | X | X |
| 3 | X | X | X |
| 4 | X | X | X |
| 5 | X | X | X |
| 6 | X | X | X |
| 7 | X | X | X |
| 8 | X | X | X |
| 9 | X | X | X |
| 10 | ○ | ○ | ○ |
| 11 | ○ | ○ | ○ |

[Note]
X: tape did not detach from the assisting tool.
○: tape detached and adhered to the skin model.

As shown in the results of the above-mentioned Table 16, it has been clarified that, when the angle of the trapezoid section in the assisting tool is the same (145°), the height of the assisting tool and the height of the side plates (height of the assisting tool+2 mm) do not affect much, and pressing for a given distance is sufficient.

b) Applicator Wherein Top of Ingot-Shape of Assisting Tool is in Parallel to Side Plates:

As applicators different from the above-mentioned a), Nos. 16, 17 wherein a tape is adhered transversely as shown in FIG. 21 were used. In addition, using the applicator of No. 1, an applicator wherein a tape is adhered transversely as shown in FIG. 21 was produced. In the same manner as in the above-mentioned Table 13, the contact area of the tape on the assisting tool to the skin was evaluated. The results are shown in the following Table 17.

TABLE 17

| pressing distance (mm) | applicator No. | | |
|---|---|---|---|
| | 1 | 16 | 17 |
| | height (mm) of trapezoid | | |
| | 0 | 1.0 | 2.5 |
| | angle of intersection of upper line and side line | | |
| | 180° | 175° | 166° |
| 1 | 0 | 0 | 0 |
| 2 | 0 | 0 | 0 |
| 3 | 0 | 0 | 0 |
| 4 | 5 | 0 | 0 |
| 5 | 7 | 0 | 0 |
| 6 | 8 | 5 | 0 |

TABLE 17-continued

| pressing distance (mm) | applicator No. | | |
|---|---|---|---|
| | 1 | 16 | 17 |
| | height (mm) of trapezoid | | |
| | 0 | 1.0 | 2.5 |
| | angle of intersection of upper line and side line | | |
| | 180° | 175° | 166° |
| 7 | | 6 | 0 |
| 8 | 10 | 8 | 2 |
| 9 | | 9 | 4 |
| 10 | 12 | 9 | 5 |
| 11 | 16 | | |
| 12 | | | 6 |
| 13 | | | |
| 14 | | | 8 |
| 15 | 14 | 11 | 8 |
| 16 | | | |

From the above results of Table 17, it has been clarified that, in the applicator Nos. 16 and 17 wherein the top of the ingot-shape of the assisting tool is in parallel to the side plates, close adhesion of the entire tape to the skin is difficult as compared to the results of Table 13.

Then, using human forearm the skin model (C) free of ink coating, the applicator was pressed in the same manner as above, and the time point when the double-faced adhesive tape peels from the assisting tool and attached and adhered to the skin model was evaluated. The results are shown in the following Table 18.

TABLE 18

| pressing distance (mm) | applicator No. | | |
|---|---|---|---|
| | 1 | 16 | 17 |
| | 0 | 1.0 | 2.5 |
| | 180° | 175° | 166° |
| 1 | X | X | X |
| 2 | X | X | X |
| 3 | X | X | X |
| 4 | X | X | X |
| 5 | ○ | X | X |
| 6 | ○ | X | X |
| 7 | | X | X |
| 8 | ○ | ○ | X |
| 9 | | ○ | X |
| 10 | ○ | ○ | X |
| 11 | ○ | | |
| 12 | | | X |
| 13 | | | |
| 14 | | | ○ |
| 15 | ○ | ○ | ○ |
| 16 | | | |

[Note]
X: tape did not detach from the assisting tool.
○: tape detached and adhered to the skin model.

As shown in the results of Table 18, it has been clarified by comparison with the results of the applicator of FIG. 8 (Table 14) that as the height of the assisting tool (supporting base for microneedle) becomes higher, a sufficient contact of the tape to the skin becomes more difficult in the applicator Nos. 16 and 17.

From the above results of the contact evaluation test with the skin by using the applicators of FIGS. 11 *a*) and *b*), it has been shown that the use of the applicator shown in FIG. 8 can afford a sufficient area of contact with the skin corresponding to the pressing distance.

c) Comparison of Human Forearm Skin Model (C) and Human Forearm:

Whether the human forearm skin model (C) is appropriate as an actual human forearm skin model was verified. Using 3 kinds of applicators (Nos. 4, 5, 14), and in the same manner as in Example 3, an applicator having a tape provided with a polypropylene circular plate (dummy microneedle) as shown in FIG. 18 was produced. In the same manner as in the aforementioned a) and using a compact desktop type testing machine (Eztest), 3 kinds of applicators were pressed against human forearm the skin model (C) and the skin of actual human forearm. In this case, during the measurement, the human forearm was under strain with a clenching fist. After release of pressing, the tape closely adhered to the skin peels off at the both ends, separated from the assisting tool and adhered to the skin. The minimum pressing distance at that time was verified by comparison. The results are shown in the following Table 19.

TABLE 19

| | applicator No. | | | | | |
|---|---|---|---|---|---|---|
| | 4 | | 5 | | 14 | |
| pressing | 2.5 mm | | 4.0 mm | | 3.0 mm | |
| distance | 166° | | 158° | | 145° | |
| (mm) | model (A) | human | model (A) | human | model (A) | human |
| 1 | X | X | X | X | X | X |
| 2 | X | X | X | X | X | X |
| 3 | X | X | X | X | X | X |
| 4 | X | X | X | X | X | X |
| 5 | X | X | X | X | X | X |
| 6 | X | X | X | X | X | X |
| 7 | ○ | ○ | X | X | X | X |
| 8 | | | X | X | X | X |
| 9 | | | ○ | X | X | X |
| 10 | | | | ○ | ○ | X |
| 11 | | | | | | ○ |
| 12 | | | | | | |

[Note]
X: tape did not detach from the assisting tool.
○: tape detached and adhered to the skin model.

As shown in the above-mentioned Table 19, it has been confirmed that human forearm skin model (B) shows almost the same behavior as a human forearm in the evaluation of applicators. Therefore, the results obtained with the human forearm skin model (B) are considered to be mostly reproducible with the skin of a human forearm.

INDUSTRIAL APPLICABILITY

In the applicator of the present invention, an ingot-shape the assisting tool is set, and a microneedle is set on the top of the assisting tool, which enables efficient puncture of the microneedle. In addition, the same tape maintaining the microneedle can be used to closely adhere the microneedle to the skin surface. Therefore, it is an applicator of a microneedle, which can be easily used by ordinary people. Thus, the device can be applied to wide uses such as self-injection of insulin etc., and vaccine injection at the time of a pandemic. Moreover, it enables perpendicular and accurate puncturing of the skin surface, and further, a microneedle can be adhered to the skin surface with ease by utilizing an adhesive tape. Therefore, practicalization of a microneedle patch, which enables convenient drug administration to the skin, can be performed by using the microneedle of the present invention.

The invention claimed is:

1. An applicator for puncturing skin comprising an assisting tool, an adhesive tape, and a microneedle, wherein the assisting tool is used as a supporting base to set the adhesive tape that carries the microneedle on an adhesive face thereof, wherein the assisting tool comprises a lower planar surface that is used to receive a pushing force, and an upper planar surface, wherein the lower planar surface has a greater surface area than that of the upper planar surface, and a pair of opposing inclined planar surfaces that extend from respective parts of a periphery of the upper planar surface to respective parts of a periphery of the lower planar surface such that a cross section of the assisting tool has a trapezoid shape, wherein an upper line and an oblique line of the trapezoid shape forms a dip angle of 130-175, and the adhesive tape is set on the assisting tool so as to extend over and contact the surface of at least a portion of the upper planar surface, at least a portion of one of the pair of opposing inclined planar surfaces, and at least a portion of another of the pair of opposing inclined planar surfaces, wherein the microneedle is placed on the upper planar surface of the assisting tool via the adhesive tape.

2. The applicator according to claim 1, wherein the assisting tool has a height of 0.5-10 mm.

3. The applicator according to claim 1, wherein the periphery of the lower planar surface and the periphery of the upper planar surface have a rectangular shape.

4. The applicator according to claim 1, which has one or more side walls at the periphery of the upper planar surface and the lower planar surface of the assisting tool, wherein the one or more side walls have a cylindrical shape, rectangular hollow section shape, or a pair of side plates.

5. The applicator according to claim 4, wherein the one or more side walls are a pair of flat plates.

6. The applicator according to claim 4, wherein a height of the assisting tool is lower than that of the one or more side walls and a tip of the microneedle does not exceed the one or more side walls.

7. The applicator according to claim 1, further comprising a resin flat plate on which the assisting tool is set, wherein the resin flat plat is in contact with the lower planar surface of the assisting tool, and one or more side walls which are placed on the same side of the resin flat plate as the assisting tool, wherein the assisting tool is housed in a concave area surrounded by the resin flat plate and the one or more side walls so as not to project over the one or more side walls.

8. The applicator according to claim 7, wherein the resin flat plate has a rectangular shape and each side of the resin flat plate has a length of 3-7 cm.

9. The applicator according to claim 7, wherein the periphery of the lower planar surface and the periphery of the upper planar surface have a rectangular shape.

10. The applicator according to claim 7, wherein the one or more side walls have a height of 2-15 mm.

11. The applicator according to claim 7, wherein the assisting tool has a height of 2-7 mm, and the height of the one or more side walls is higher by 2-3 mm than that of the assisting tool.

12. The applicator according to claim 9, wherein the dip angle is 145-175°.

13. The applicator according to claim 1, wherein the assisting tool has a shape of a circular truncated cone or a polygonal truncated pyramid.

14. A method for puncturing skin with a microneedle, comprising:
   providing the applicator according to claim 1,
   pressing the applicator against the skin to puncture the skin with the microneedle and simultaneously to adhere the microneedle to the skin surface with the adhesive tape, and
   separating the assisting tool off the skin while keeping the adhesive tape carrying the microneedle adhered to the skin.

* * * * *

UNITED STATES PATENT AND TRADEMARK OFFICE
CERTIFICATE OF CORRECTION

PATENT NO. : 9,750,924 B2
APPLICATION NO. : 13/574496
DATED : September 5, 2017
INVENTOR(S) : Kobayashi et al.

Page 1 of 1

It is certified that error appears in the above-identified patent and that said Letters Patent is hereby corrected as shown below:

On the Title Page

(75) Inventors:
"Katsunori Kobayashi, Kagawa (JP)" should read "Katsunori Kobayashi, Higashikagawa (JP)"
"Hidetoshi Hamamoto, Kagawa (JP)" should read "Hidetoshi Hamamoto, Higashikagawa (JP)"

On Page 2 (56) FOREIGN PATENT DOCUMENTS:
"WO 2007124411" should read "WO 2007/124411"

In the Claims

Claim 1, Column 24, Line 15, "130-175" should read "130-175°"

Signed and Sealed this
Twenty-seventh Day of March, 2018

Andrei Iancu
*Director of the United States Patent and Trademark Office*